US010828235B2

(12) United States Patent
Limaye et al.

(10) Patent No.: US 10,828,235 B2
(45) Date of Patent: Nov. 10, 2020

(54) SHORT INJECTION LENGTH SYRINGE

(71) Applicant: Becton, Dickinson and Company, Franklin Lakes, NJ (US)

(72) Inventors: Amit Limaye, Wayne, NJ (US); Kevin O'Hara, Ramsey, NJ (US); David Schiff, Highland Park, NJ (US); Jesse Gala, Summit, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 689 days.

(21) Appl. No.: 15/363,776

(22) Filed: Nov. 29, 2016

(65) Prior Publication Data
US 2017/0151129 A1 Jun. 1, 2017

Related U.S. Application Data

(60) Provisional application No. 62/261,100, filed on Nov. 30, 2015.

(51) Int. Cl.
*A61J 1/20* (2006.01)
*A61M 5/178* (2006.01)
(Continued)

(52) U.S. Cl.
CPC .......... *A61J 1/2096* (2013.01); *A61J 1/2065* (2015.05); *A61M 5/1782* (2013.01);
(Continued)

(58) Field of Classification Search
CPC ................. A61J 1/2065; A61J 1/2096; A61M 2005/3114; A61M 5/178; A61M 5/1782;
(Continued)

(56) References Cited

U.S. PATENT DOCUMENTS 6,494,865 B1 12/2002 Alchas
6,569,123 B2 5/2003 Alchas et al.
(Continued)

FOREIGN PATENT DOCUMENTS

CN 204219528 U 3/2015
CN 104474611 A 4/2015
(Continued)

OTHER PUBLICATIONS

BD, Discover how BD Insulin Syringes and Pen Needles can help ease your Diabetes Injection Experience Brochure.
(Continued)

*Primary Examiner* — Kai H Weng
(74) *Attorney, Agent, or Firm* — Dickinson Wright PLLC

(57) ABSTRACT

A syringe includes a syringe body having a syringe barrel for receiving and administering a medicament, a hollow needle fluidly communicating with the syringe barrel, and a needle adapter disposed on the syringe body. An outer diameter of the needle adapter is wider than an outer diameter of the syringe barrel, and a distal surface of the needle adapter is substantially flat. The needle adapter facilitates a flush alignment of the distal surface of the needle adapter with at least one of a vial stopper and a vial stopper holder of a medicament vial to ensure that a tip of the needle is properly inserted into the vial to aspirate the medicament within the vial.

25 Claims, 47 Drawing Sheets

(51) Int. Cl.
*A61M 5/32* (2006.01)
*A61M 5/34* (2006.01)
*A61M 5/31* (2006.01)

(52) U.S. Cl.
CPC ........ *A61M 5/3213* (2013.01); *A61M 5/3293* (2013.01); *A61M 5/349* (2013.01); *A61M 5/178* (2013.01); *A61M 5/3202* (2013.01); *A61M 2005/3114* (2013.01)

(58) Field of Classification Search
CPC .............. A61M 5/3202; A61M 5/3213; A61M 5/3293; A61M 5/349
See application file for complete search history.

(56) References Cited

U.S. PATENT DOCUMENTS

| | | | |
|---|---|---|---|
| 6,569,143 | B2 | 5/2003 | Alchas et al. |
| 6,689,118 | B2 | 2/2004 | Alchas et al. |
| 6,776,776 | B2 | 8/2004 | Alchas et al. |
| 6,843,781 | B2 | 1/2005 | Alchas et al. |
| 7,108,679 | B2 | 9/2006 | Alchas |
| 7,241,275 | B2 | 7/2007 | Alchas et al. |
| 7,250,036 | B2 | 7/2007 | Alchas |
| 8,262,641 | B2 | 9/2012 | Vedrine et al. |
| 8,267,890 | B2 | 9/2012 | Alchas et al. |
| 8,827,956 | B2 | 9/2014 | Banik et al. |
| 2002/0045858 | A1 | 4/2002 | Alchas et al. |
| 2004/0097882 | A1 | 5/2004 | Dibiasi et al. |
| 2011/0092952 | A1* | 4/2011 | Voellmicke ........... A61M 5/008 604/506 |
| 2014/0276649 | A1* | 9/2014 | Ivosevic ............... A61J 1/2096 604/533 |
| 2015/0094666 | A1* | 4/2015 | Bates ................. A61M 5/3202 604/197 |

FOREIGN PATENT DOCUMENTS

| | | |
|---|---|---|
| JP | 2008168119 | 7/2008 |
| JP | 2010233718 | 10/2010 |
| JP | 2011-519681 A | 7/2011 |
| JP | 2012-10930 A | 1/2012 |
| JP | 2012508058 | 4/2012 |
| JP | 2004283554 | 10/2014 |
| JP | 2015504716 | 2/2015 |
| WO | WO-2010053570 A1 | 5/2010 |
| WO | WO-2013155005 A1 | 10/2013 |

OTHER PUBLICATIONS

BD. Hypodermic Product Catalog—The Basis for Selection of Your Medication Delivery Device Needs, Apr. 2006.

\* cited by examiner

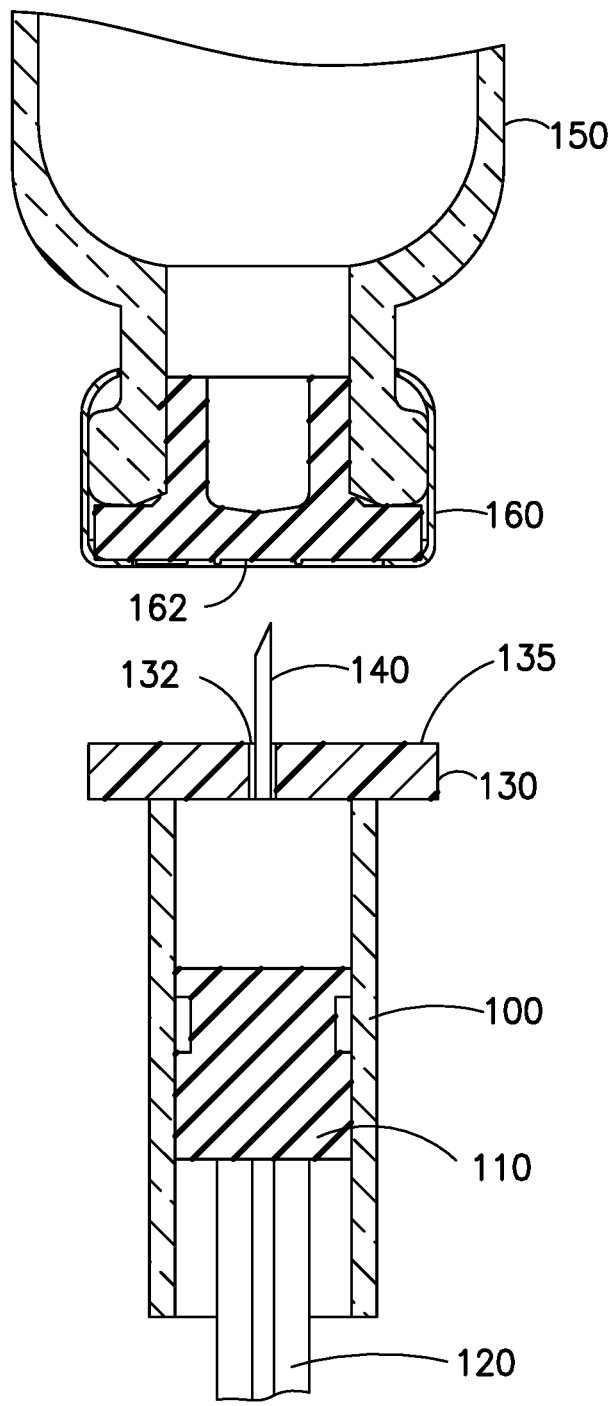
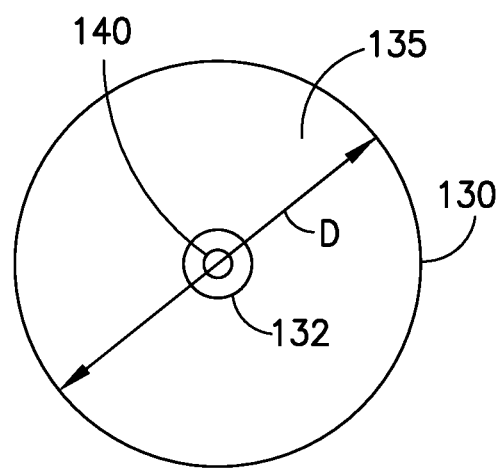
FIG.1
FIG.2

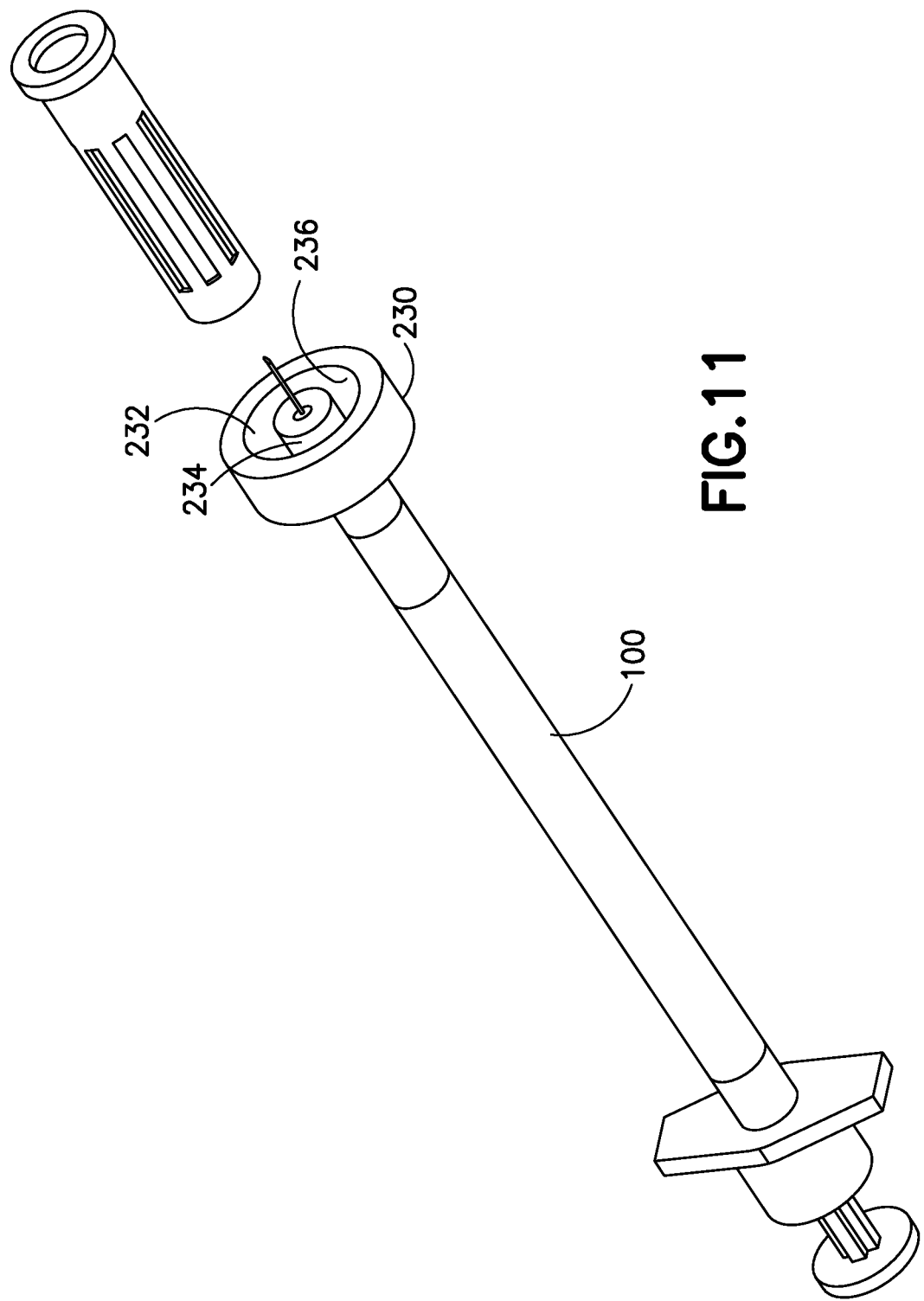

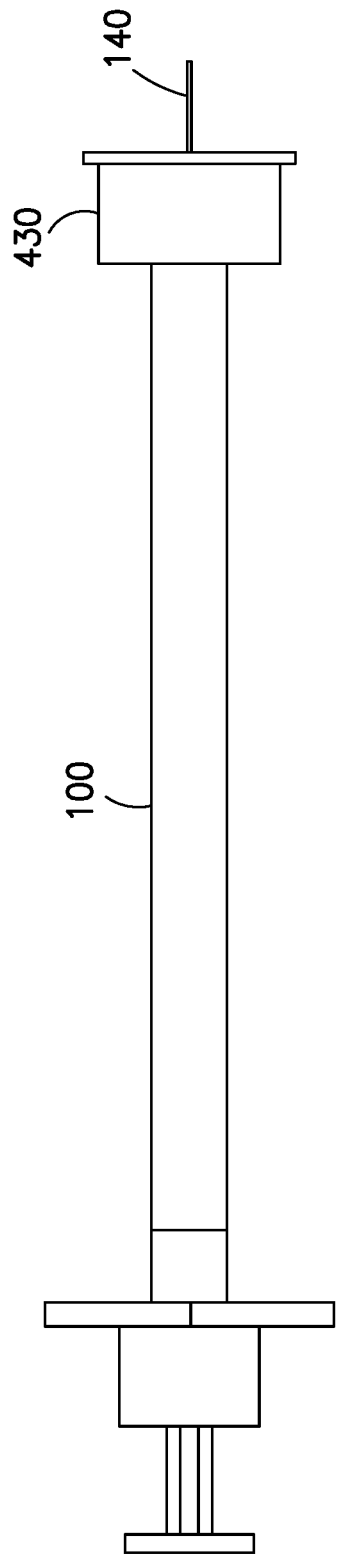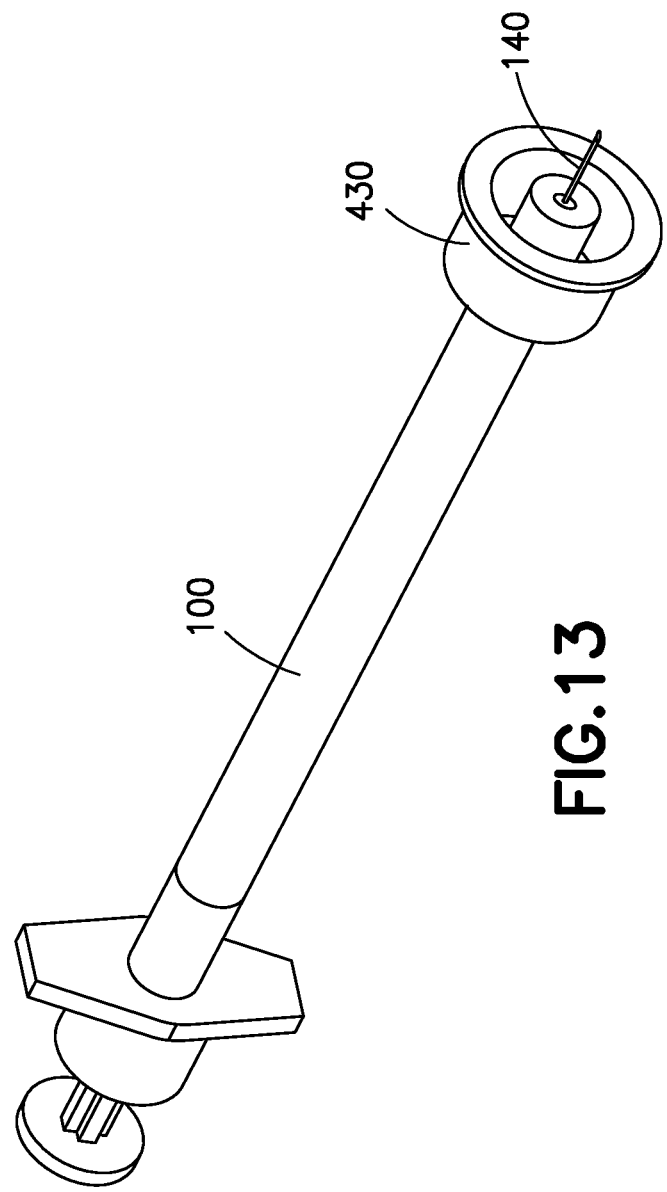

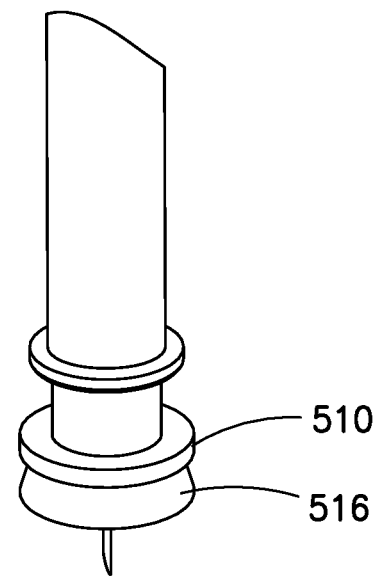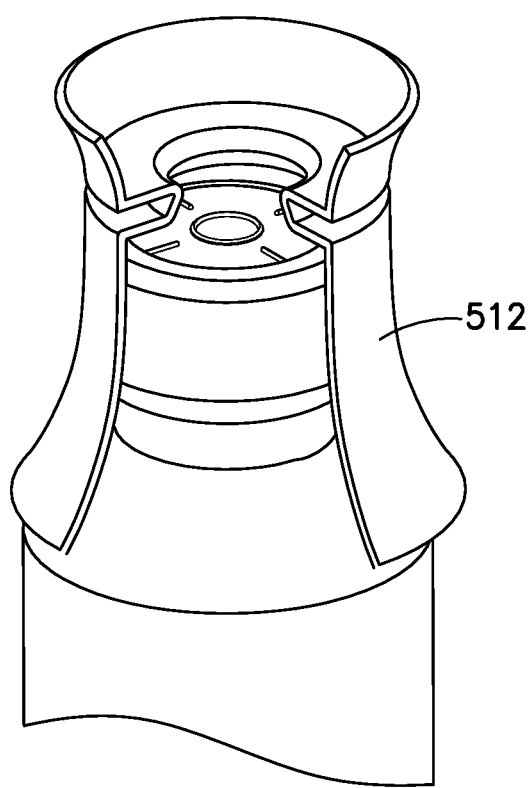
FIG.24

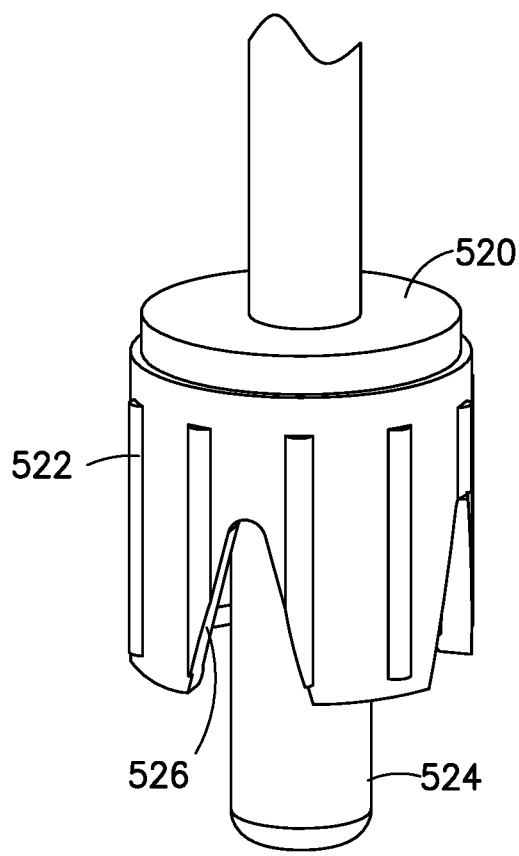
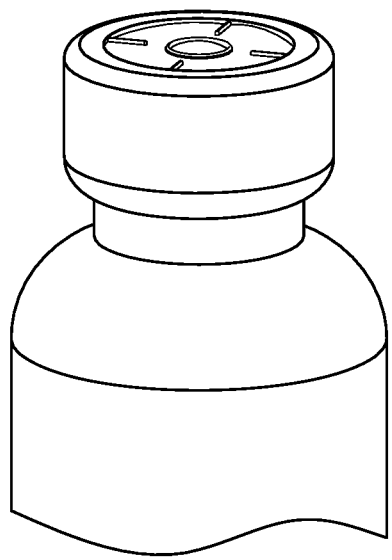
FIG.25

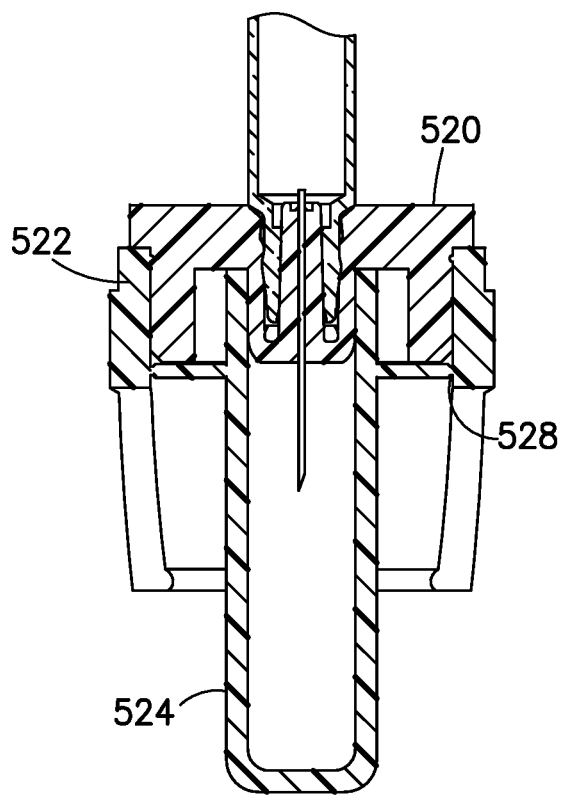
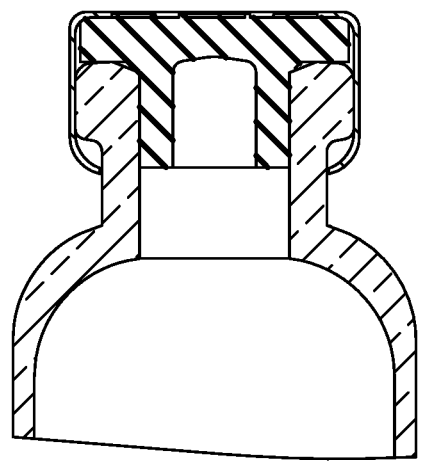
FIG.26

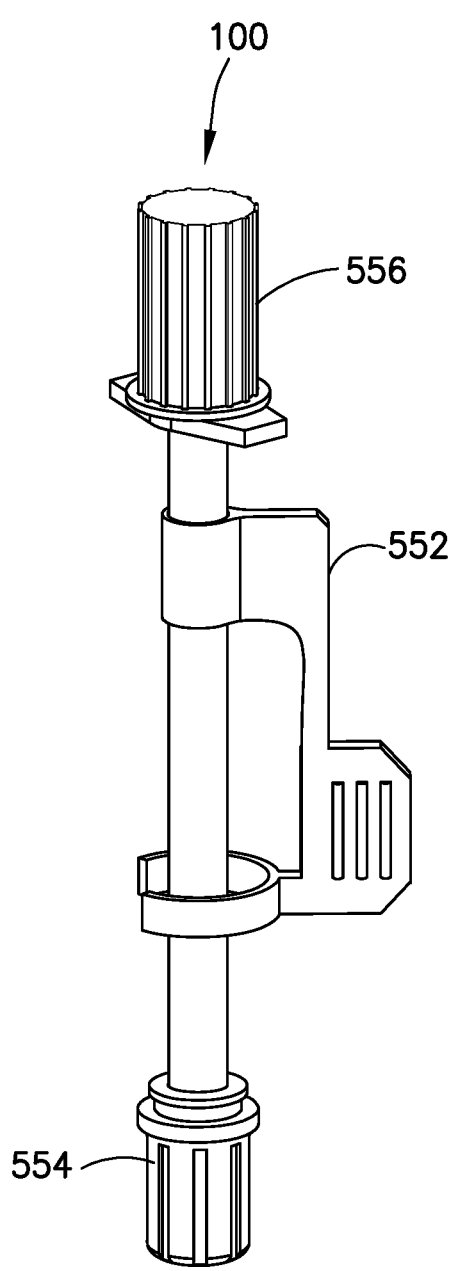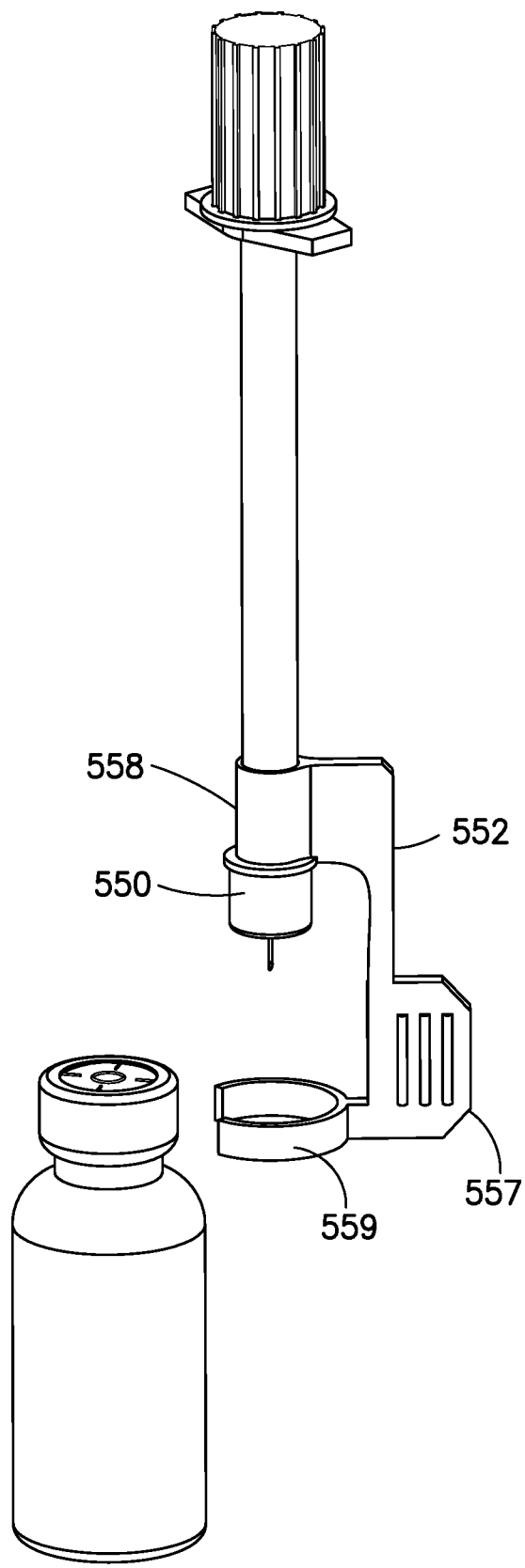
FIG.35
FIG.36

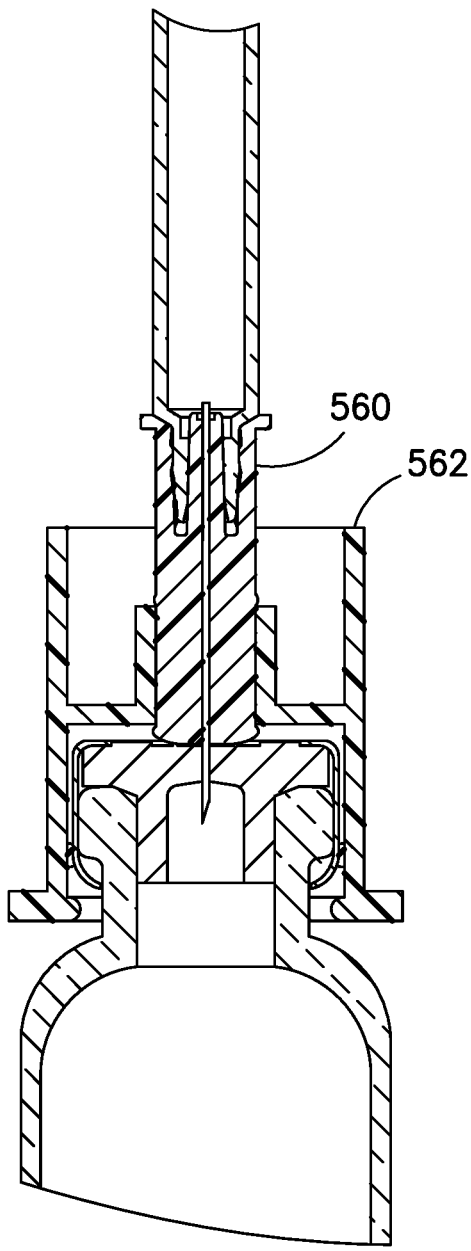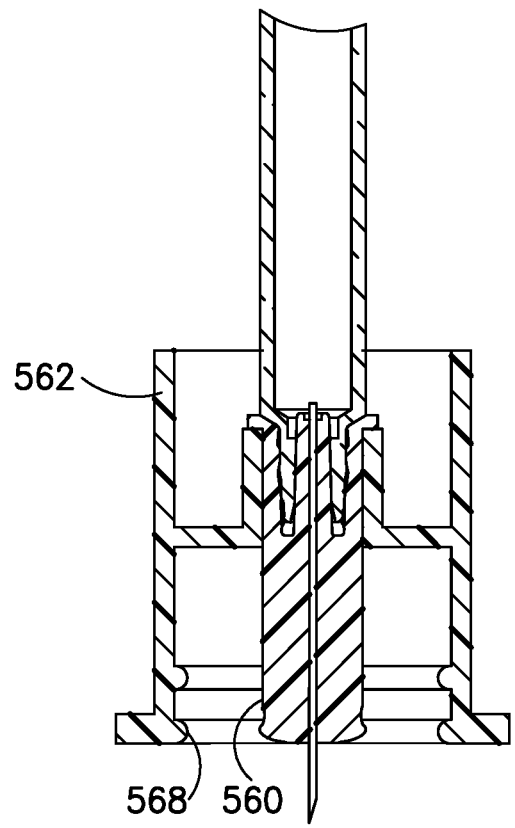
FIG.43
FIG.44

SHORT INJECTION LENGTH SYRINGE

CROSS-REFERENCE TO RELATED APPLICATION

This application claims priority under 35 USC § 119(e) from U.S. Provisional Patent Application Ser. No. 62/261,100, filed on Nov. 30, 2015, the disclosure of which is incorporated herein by reference in its entirety.

FIELD OF THE INVENTION

The present invention relates generally to the filling of delivery devices for delivering substances such as drugs, vaccines and the like, and more specifically relates to a drug delivery system and device having a needle which has a relatively short protrusion length. More specifically, the present invention relates to a method and apparatus for filling a subcutaneous insulin delivery syringe from a vial using a shortened needle.

BACKGROUND OF THE INVENTION

As advances in understanding the delivery of drugs proceed, the benefits of shorter needle lengths are being realized. The use of shorter needle lengths is recommended as safe, effective and preferred for improved comfort and less pain. In fact, shorter needle lengths are recommended by healthcare providers and preferred by patients for a more comfortable injection. Shorter needle lengths help deliver medicament such as insulin to the subcutaneous tissue (the fatty layer just under the skin) and reduce the risk of injecting into muscle. Intramuscular injections are painful, make insulin work faster, and may increase the risk of low blood sugar (hypoglycemia).

A shorter needle has many benefits including allowing injection with one hand and also allowing a straight-in injection, which gives the flexibility to use any injection site. This can make site rotation easier and offer more discreet injections when in social situations. The shorter needle also reduces the risk of painful injections into muscle. With the shorter needle a user can inject straight in at 90 degrees and no skin pinch-up or fold is needed.

It is difficult to use a delivery device having a shorter needle length to aspirate a drug substance into a syringe from a multi-use vial. A shorter needle must be inserted into the vial at a 90 degree angle to ensure full penetration of the vial stopper. Insertion at a 90 degree angle, however, is not always achieved. In some cases, the needle is inserted at an angle other than 90 degrees, and as a result, the needle can enter the side of the well of the stopper where the well acts like a clog, or the tip of the needle becomes embedded in the rubber septum portion of the stopper. Thus, there are shortcomings that prevent administering a subcutaneous injection using a needle shorter than a "standard" length needle and a multi-use vial. It would be advantageous to have a drug delivery device with a shorter needle that is capable of accessing substances stored in multi-dose vials and delivering such substances into the subcutaneous region of the skin without encountering the shortcomings described above.

Accordingly, a need exists for an adapter for shorter needle syringes that facilitate subcutaneous medicament injection and accessing medicament stored in multi-dose vials.

SUMMARY OF EMBODIMENTS OF THE INVENTION

The foregoing and/or other aspects of the present invention are achieved by providing a syringe includes a syringe body having a syringe barrel for receiving and administering a medicament, a hollow needle fluidly communicating with the syringe barrel, and a needle adapter disposed on the syringe body. An outer diameter of the needle adapter is wider than an outer diameter of the syringe barrel, and a distal surface of the needle adapter is substantially flat. The needle adapter facilitates a flush alignment of the distal surface of the needle adapter with at least one of a vial stopper and a vial stopper holder of a medicament vial to ensure that a tip of the needle is properly inserted into the vial to aspirate the medicament within the vial.

The foregoing and/or other aspects of the present invention are also achieved by providing a method of preparing a syringe for injection, the syringe including a syringe body having a syringe barrel, a hollow needle communicating with the syringe barrel, and a needle adapter disposed on the syringe body, an outer diameter of the needle adapter being wider than an outer diameter of the syringe barrel, and a distal surface of the needle adapter being substantially flat. The method includes engaging the distal surface of the needle adapter flush against a vial stopper holder of a medicament vial to ensure that a tip of the needle is properly inserted into the vial to aspirate the medicament within the vial, aspirating the medicament within the vial through the needle into the syringe barrel, and disengaging the distal surface of the needle adapter from the vial stopper holder.

Additional and/or other aspects and advantages of the present invention will be set forth in the description that follows, or will be apparent from the description, or may be learned by practice of the invention.

BRIEF DESCRIPTION OF THE DRAWINGS

The above and/or other aspects and advantages of embodiments of the invention will be more readily appreciated from the following detailed description, taken in conjunction with the accompanying drawings, in which:

FIG. 1 is a cross-sectional view of a short injection length syringe and vial according to an exemplary embodiment of the present invention;

FIG. 2 is an enlarged distal end view of the syringe of FIG. 1;

FIGS. 9-11 are elevational and perspective views of the short injection length syringe of FIG. 3;

FIGS. 12 and 13 are elevational and perspective views of another exemplary embodiment of the short injection length syringe, utilizing a separate snap-fit needle hub;

FIGS. 22-24 are partial elevational views of the syringe of FIG. 21 and a medicament vial;

FIGS. 25 and 26 are partial elevational and cross-sectional views of a syringe in accordance with another exemplary embodiment of the present invention;

FIGS. 35-39 are elevational and partial elevational views of a syringe in accordance with another exemplary embodiment of the present invention, and the filling operation thereof;

FIGS. 41-44 are partial cross-sectional views of the syringe of FIG. 40 illustrating operation thereof;

DETAILED DESCRIPTION OF EMBODIMENTS OF THE PRESENT INVENTION

Figures 3, 4:
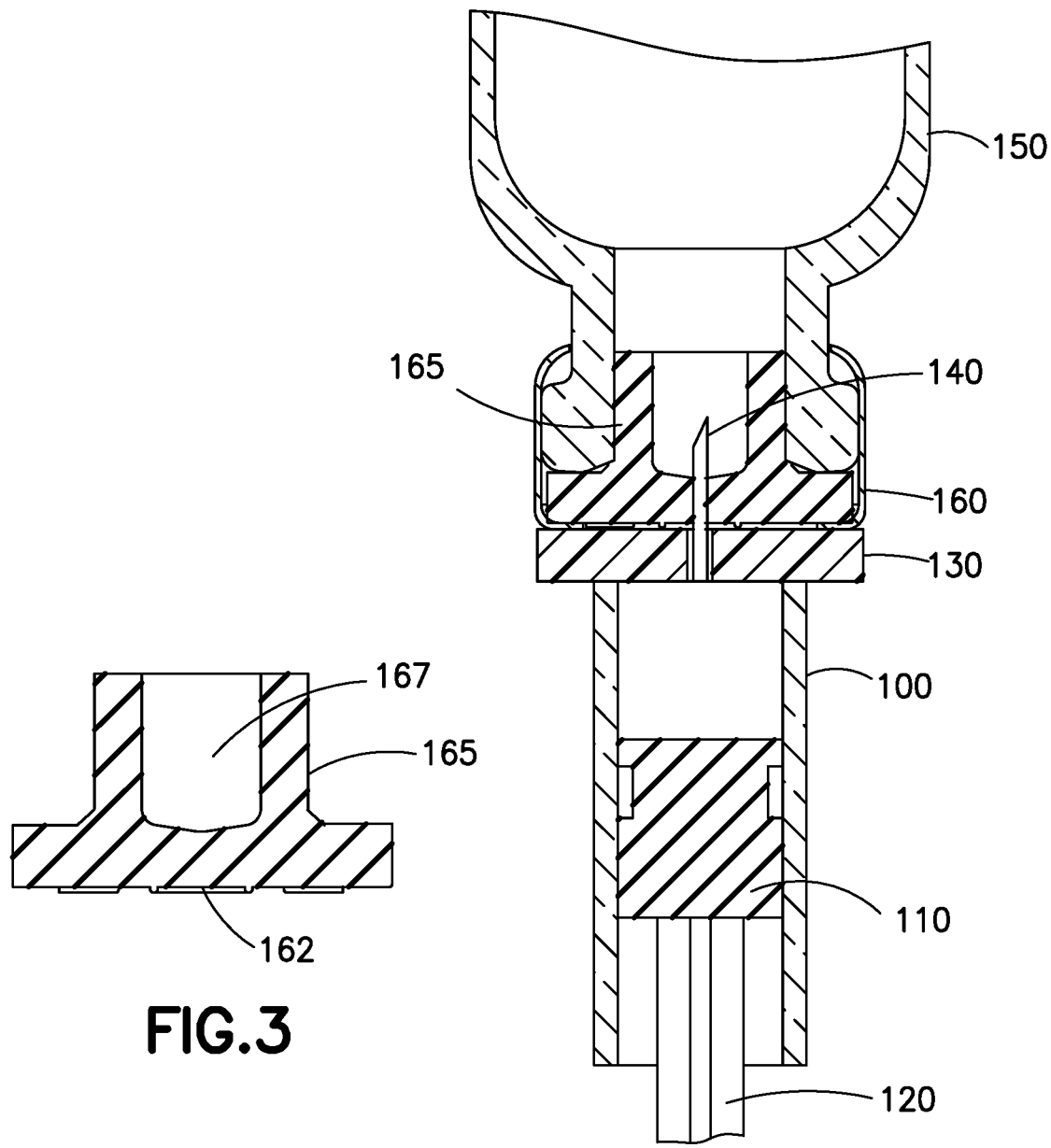
FIG. 3 is a cross-sectional view of the stopper used in the vial of FIG. 1.
FIG. 4 is a cross-sectional view of the short injection length syringe of FIG. 1 inserted into the medicament vial.

Reference will now be made in detail to embodiments of the present invention, which are illustrated in the accompanying drawings, wherein like reference numerals refer to like elements throughout. The embodiments described herein exemplify, but do not limit, the present invention by referring to the drawings.

It will be understood by one skilled in the art that this disclosure is not limited in its application to the details of construction and the arrangement of components set forth in the following description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as "up", "down", "bottom", and "top" are relative, and are employed to aid illustration, but are not limiting.

In a first exemplary embodiment of the present invention, as shown in FIG. 1, a subcutaneous insulin syringe 100 with a staked (fixed or non-detachable) needle is provided. The insulin syringe 100 has a plunger 120 disposed at a first end and a hollow injection needle 140 of shorter than standard length (preferably 3.5 to 5 mm as opposed to the more conventional 8 to 16 mm length) rigidly fixed at the second end. The needle 140 is sharpened at its distal end and may be of any appropriate gauge (preferably 31, 32 or 33 gauge). In accordance with one feature, a specially shaped needle adapter 130 serving as a hub for the needle 140 is disposed at the distal end of the syringe 100. As shown in FIG. 1, the Medicament can be drawn into and administered from the syringe 100 using a vial. A stopper 110 is connected to the plunger 120 and moved through the syringe 100 by the plunger 120 to aspirate or dispense the medicament.

As illustrated in FIG. 2, the needle adapter 130 has a flat external distal surface 135 and an outer diameter D. The needle 140 is received in a hole 132 in the needle adapter 130 and secured therein by means of an adhesive. Outer diameter D is wider than that of the syringe barrel 102 and is similar to the outer diameter of a metal crimp ring or vial stopper holder 160 on an insulin medicament vial 150. One skilled in the art will appreciate that a vial stopper holder other than a crimp ring can be employed with embodiments of the present invention. For brevity, however, the crimp ring will be used as an illustrative example of a vial stopper holder. The medicament vial 150 is sealed by a rubber stopper 165 that is surrounded and held in place by the metal crimp ring 160. FIG. 3 illustrates the rubber stopper 165 including a septum portion 162 that is intended for penetration by a syringe needle. A user can orient the syringe 100 such that the outer diameter of the needle adapter 130 generally aligns with the outer diameter of the metal crimp ring 160, as shown in FIG. 4, upon insertion of the syringe needle 140 into the medicament vial stopper 165.

Alignment of the features of the vial 150 and the syringe 100, namely the metal crimp 160 and the needle adapter 130 of the syringe 100, can be achieved either visually or using tactile feedback. As shown in FIG. 4, this alignment ensures that the needle 140 enters the central region of the septum 162 perpendicularly, and that a dose can be drawn from the vial without the tip of the needle 140 being embedded inside the side portion of the stopper well 167. The alignment ensures that the user has properly inserted the needle 140 and can be used to reinforce the straight-in insertion approach during the subsequent injection. It will be understood that this alignment need not be precise to realize the desired advantages, nor is it essential that the outer diameters of the needle adapter 130 and crimp ring 160 be the same (although this may be preferred in some embodiments).

Figure 5:
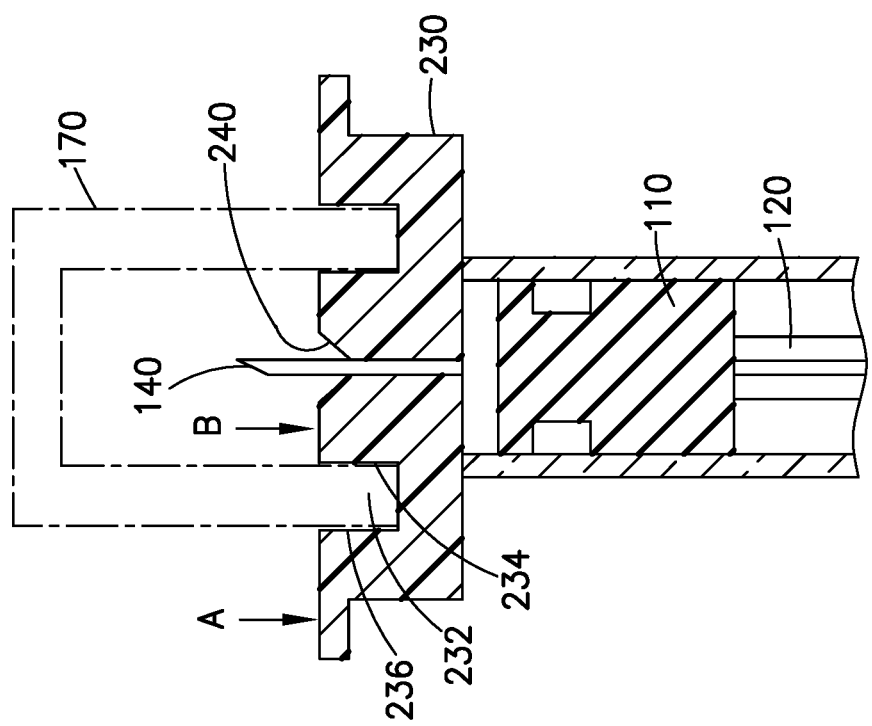
FIG. 5 is a cross-sectional view of a short injection length syringe in accordance with another exemplary embodiment of the present invention.

An alternative needle adapter 230 is illustrated in FIG. 5. This needle adapter 230 includes an annular well 232 in which a needle shield 170 can be installed. The annular well 232 includes an inner wall 234 and an outer wall 236. The shield is retained between the inner and outer walls 234, 236 by an interference fit.

Figure 6:
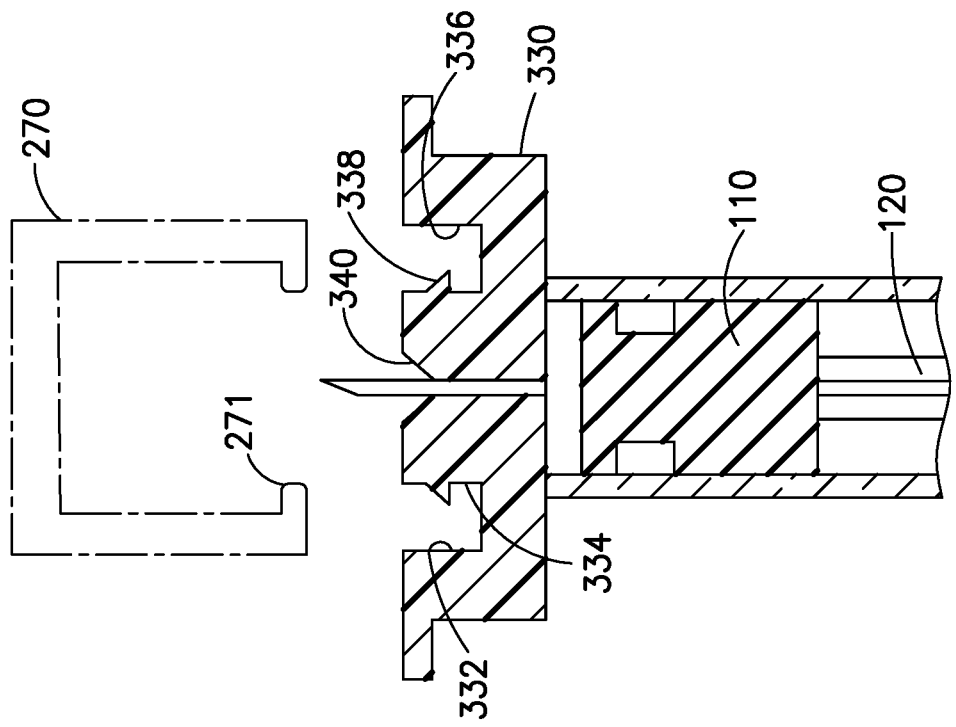
FIG. 6 is a cross-sectional view of a short injection length syringe including a retention ring in accordance with another exemplary embodiment of the present invention.

As illustrated in FIG. 6, an alternative shield 270 can attach to the inner 334 and outer 336 walls of the well 332 via a retention ring 338 which also creates a tortuous path for providing a sterility barrier. The retention ring 338 protrudes from inner wall 334 and engages with gripping features 271 of the needle shield 270, as shown in FIG. 6. In other embodiments, the retention ring 338 can protrude from the outer wall 336 and the configuration of the needle shield 270 can be modified accordingly.

A recessed adhesive well 240 or 340 allows the needle to be attached with no raised adhesive bead. The flat and wide needle adapter 130, 230 or 330 allows for control of depth of insertion of the syringe needle into the user's skin as well as into the vial. A 3.5 mm needle on this syringe will have very low probability of undesirable intradermal injection. Pressing the flat wide needle adapter 130, 230 or 330 against a user's skin reduces probability of an intradermal injection.

The hub portion 130, 230, 330 of the syringe can be made separately such that a snap-fit to the syringe body 101 can be used. The needle 140 can be permanently attached to the hub 130, 230, 330 as shown in the drawings, or it can be detachable via a Luer lock or Luer slip fitting.

In FIG. 5, surface B of the needle adapter 230 can be protruded or recessed in relation to surface A so as to provide the ability to change the location of the subcutaneous deposition of insulin. Surfaces A and/or B can have additional features to further facilitate this. The embodiment of FIG. 6 can be configured similarly.

The syringe described herein is intended to enable small injection length needles, such as 4 mm and 5 mm needles, to reliably draw a dose from insulin vials having different stopper geometries. As illustrated in FIGS. 1-6, the bottoming out of the flat wide portion of the needle adapter onto the vial crimp 160 along with the alignment mechanism will ensure that the tip of the needle 140 penetrates the septum portion 162 to access the liquid medicament and does not become embedded in the rubber material of the stopper 165. The septa 162 of most vial stoppers 165 are about 2 mm thick. The location of the tip of the needle 140 inside the vial, as illustrated in FIGS. 1 and 4, will also allow the user to draw out most of the medicament without having to reposition or draw out the needle to access the liquid medicament, thereby allowing for complete usage of the drug in the multi-dose vial and reducing the waste of expensive medication.

Figures 7, 8:
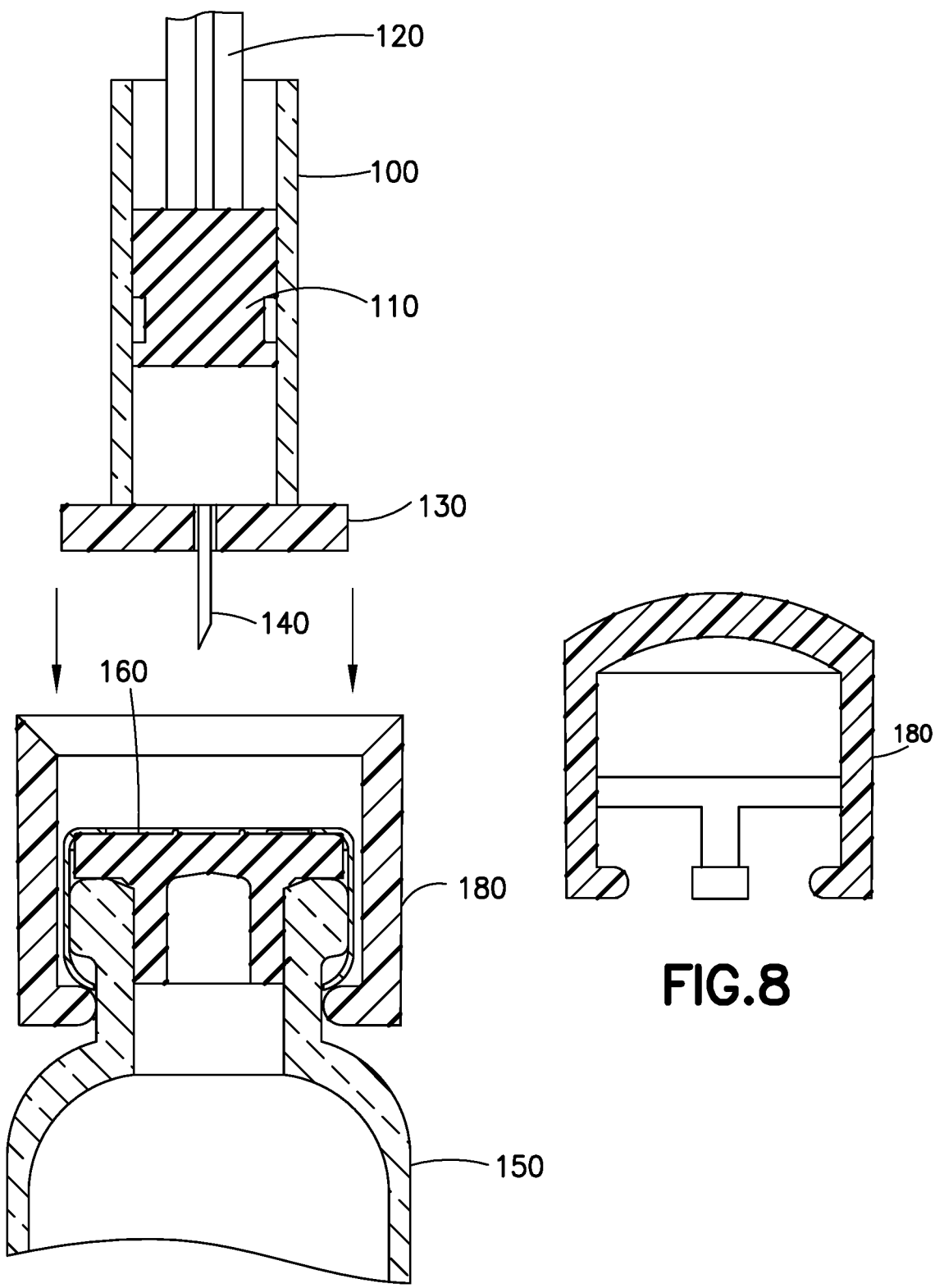
FIG. 7 is a cross-sectional view of a short injection length syringe assembly according to another exemplary embodiment of the present invention.
FIG. 8 is a cross-sectional view of a guided insertion aid in accordance with another exemplary embodiment of the present invention.

A guided insertion aid or vial adapter 180, as shown in FIGS. 7 and 8, can be provided with the syringe as an additional means of ensuring that the syringe assembly 100 is inserted centrally and perpendicularly into the vial stopper 165 as intended. While this vial adapter is not required for correct functioning of the syringe 100 of the current embodiment, it will further ensure correct insertion and may be useful for people with compromised vision or dexterity.

The vial adapter 180 is a cylindrical member that can snap onto the neck or vial stopper holder of a medicament vial 150 and can remain on the vial 150. It should be noted that the shape and size of the vial adapter can be adjusted to make it easier to use and easier to swab the vial top 160.

In addition to assisting with the syringe 100 of the present invention, the vial adapter is usable with other syringes used by the user. As such, it is capable of being left on the vial without interfering with the normal use of the vial.

Figure 9:
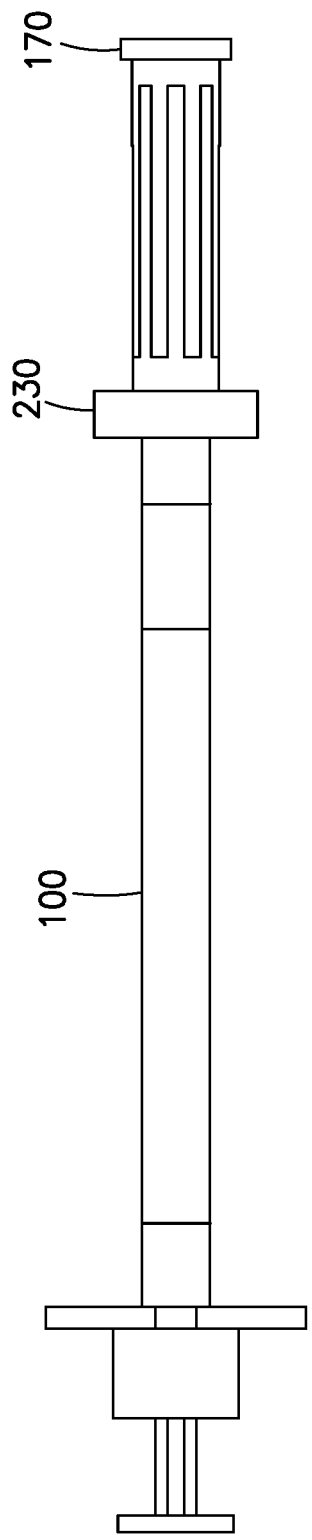
Figure 10:
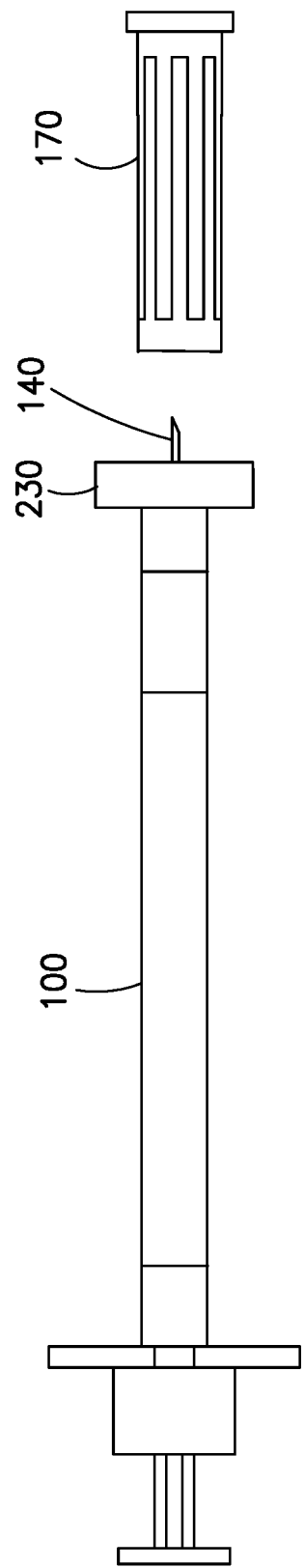
Figure 14:
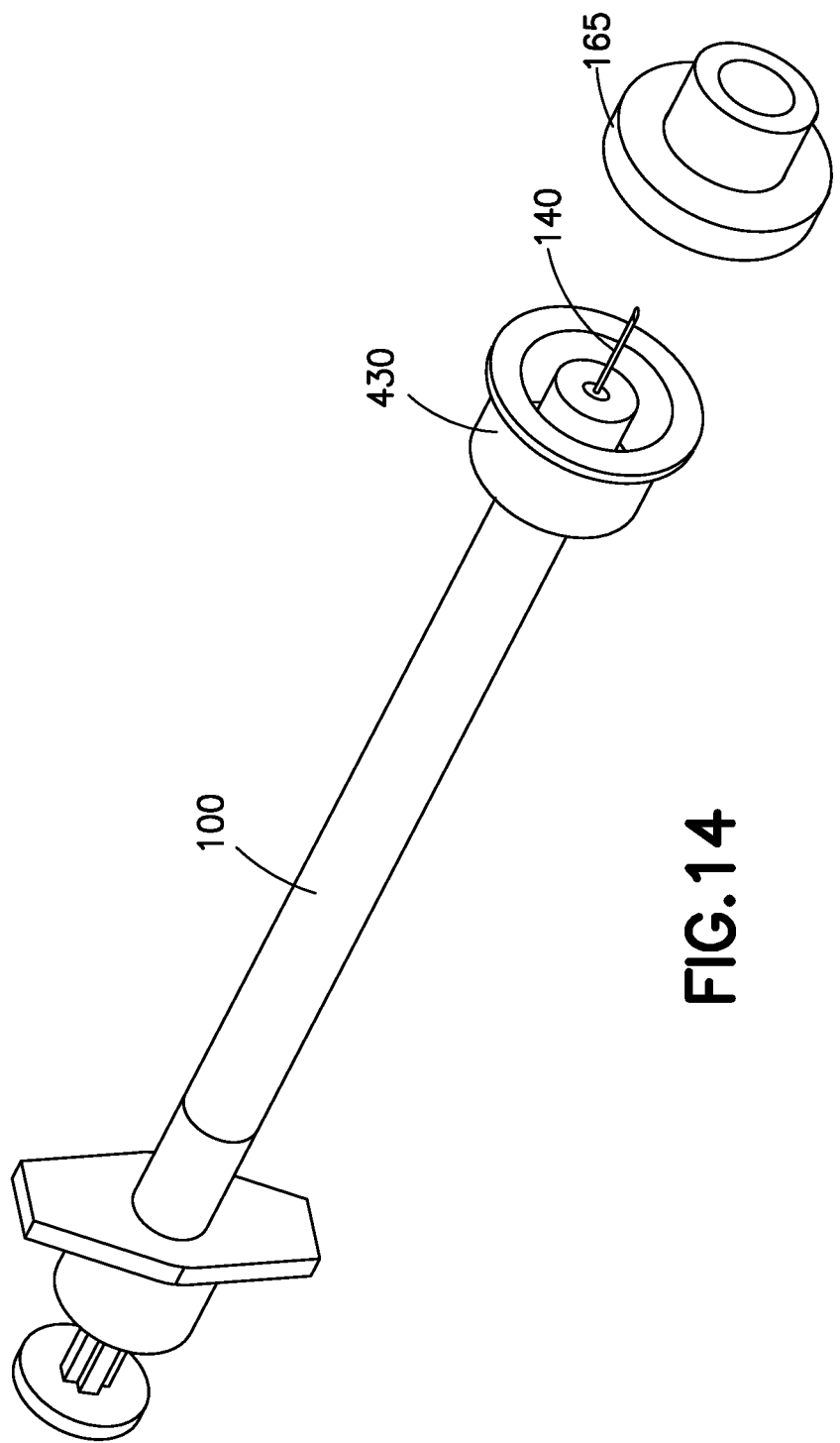
FIGS. 14 and 15 are perspective and cross-sectional views of the short injection length syringe of FIGS. 12 and 13, illustrating the alignment of the syringe with a vial stopper.
Figure 15:
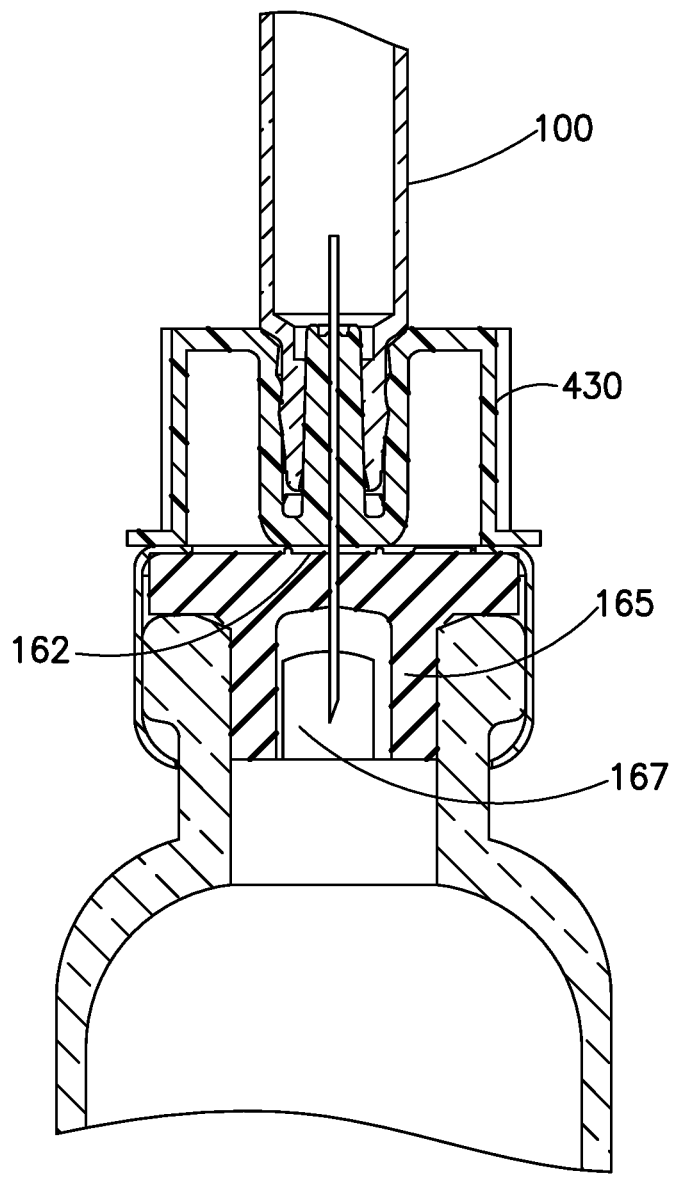

FIGS. 9-15 provide additional views of exemplary embodiments of the invention. FIGS. 9-11 illustrate the embodiment of FIG. 5 in which the needle 140 is staked into the syringe body 101 with a flat end. The needle 140 is glued directly into the syringe end. In FIGS. 12 and 13, the needle 140 is staked into a separate hub with a flat end. The needle 140 is glued into the hub and the hub is then snap fit into the syringe body 101. FIG. 14 illustrates the alignment of the syringe 100 of FIGS. 12 and 13 with a vial stopper 165. FIG. 15 is a cross-sectional view of the syringe 100 and the stopper 165 showing insertion of the needle 140 through the septum area 162 of the stopper 165 and into the well area 167 of the stopper 165.

Figure 16:
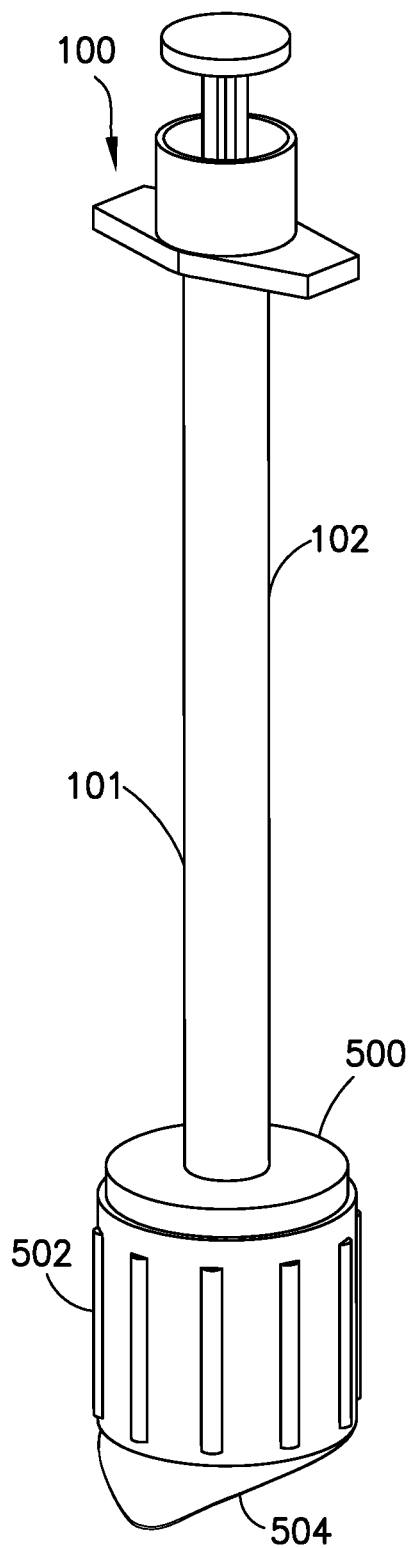
FIGS. 16 and 17 are elevational and partial cross-sectional views of a syringe in accordance with another exemplary embodiment of the present invention.
Figure 17:
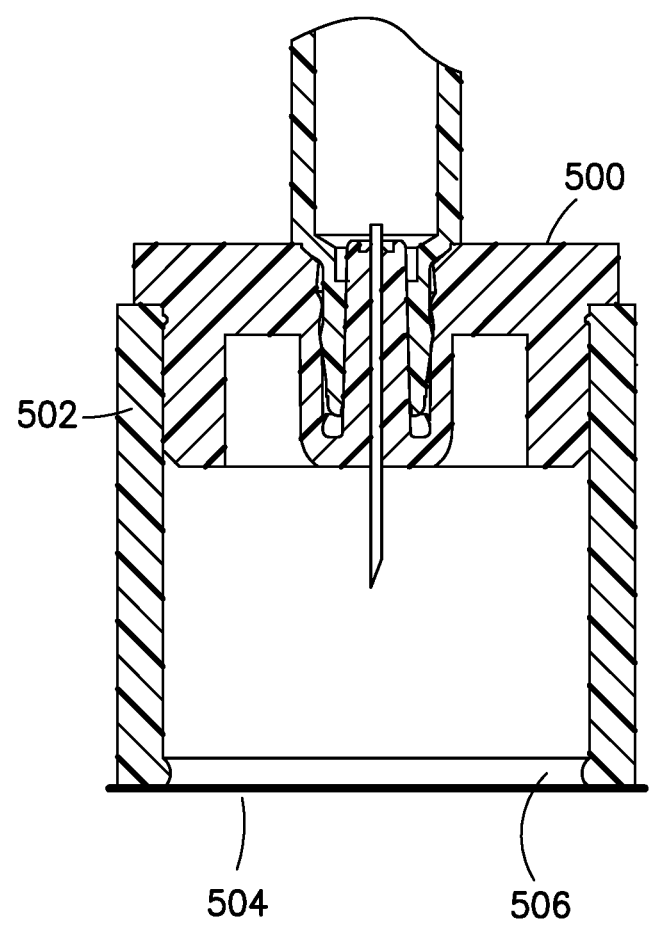

FIGS. 16 and 17 are elevational and partial cross-sectional views of another exemplary embodiment of the present invention. The needle adapter 500 is disposed on the distal-most end of the syringe body 101, and a vial adapter 502 removably disposed on the needle adapter 500. More specifically, in this embodiment, the vial adapter 502 is a sleeve 502 that is initially removably connected to a distal end of the needle adapter 500 at a first end of the sleeve 502, and is connectable to the medicament vial 150 at a second, opposite end of the sleeve 502.

A peel tab 504 is removably disposed on the distal end of the vial adapter 502. Together with the tortuous path of the connection between the vial adapter 502 and the needle adapter 500, the peel tab 504 maintains sterility of the needle 140 prior to use.

Figure 18:
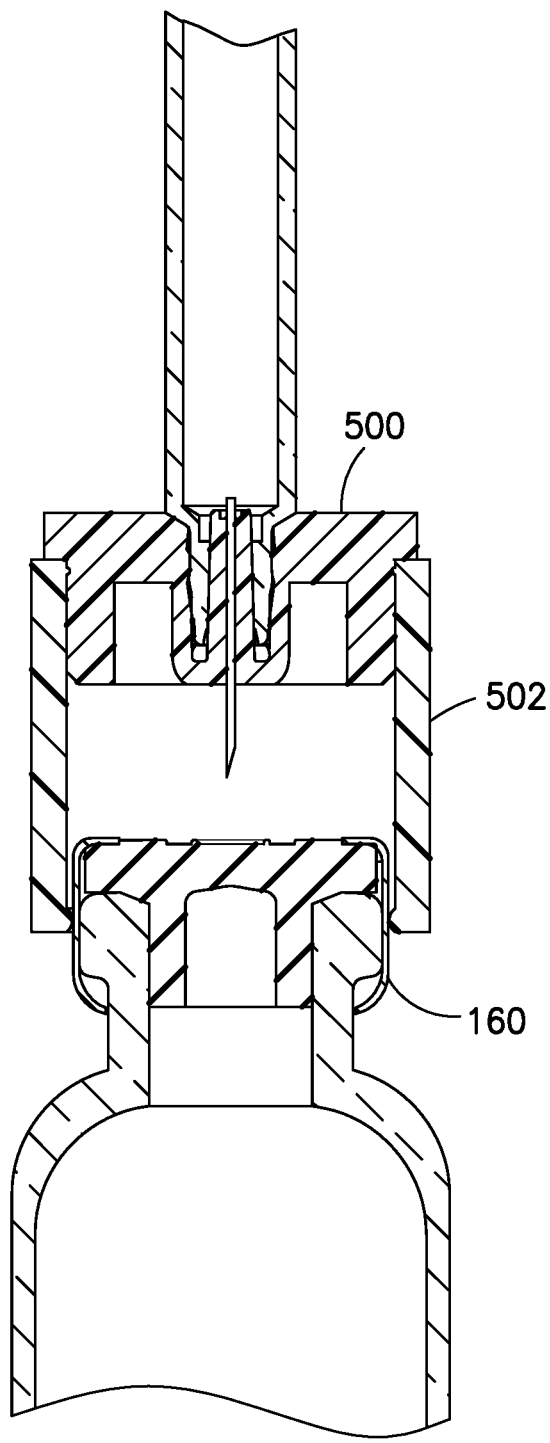
FIGS. 18 and 19 are partial cross-sectional views and FIG. 20 is an elevational view of the process of filling the syringe of FIG. 16.
Figure 19:
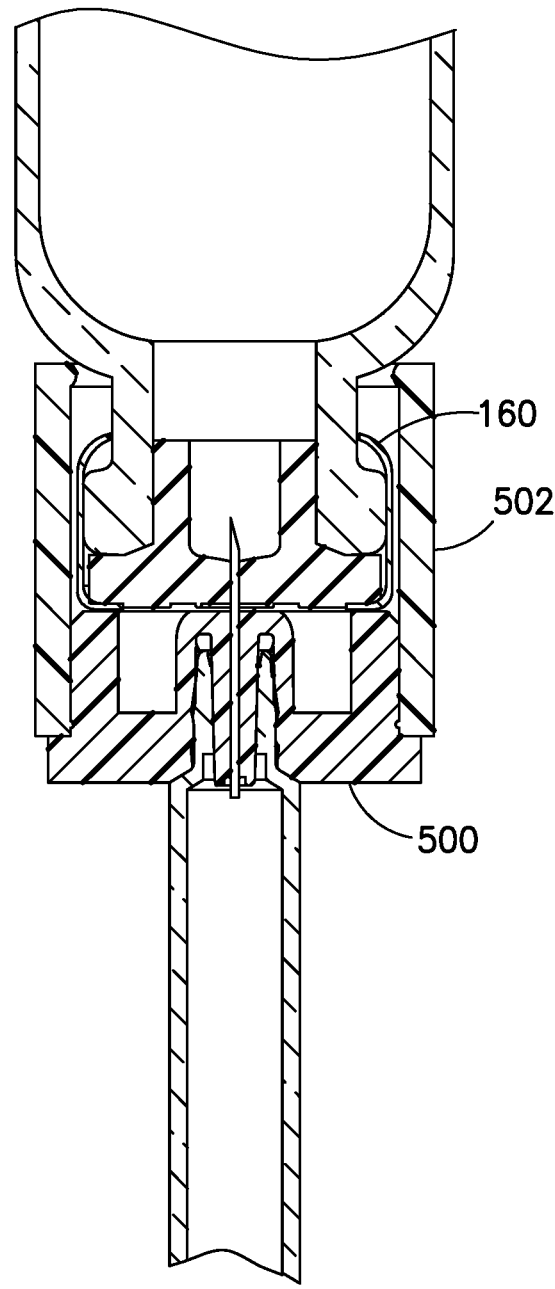
Figure 20:
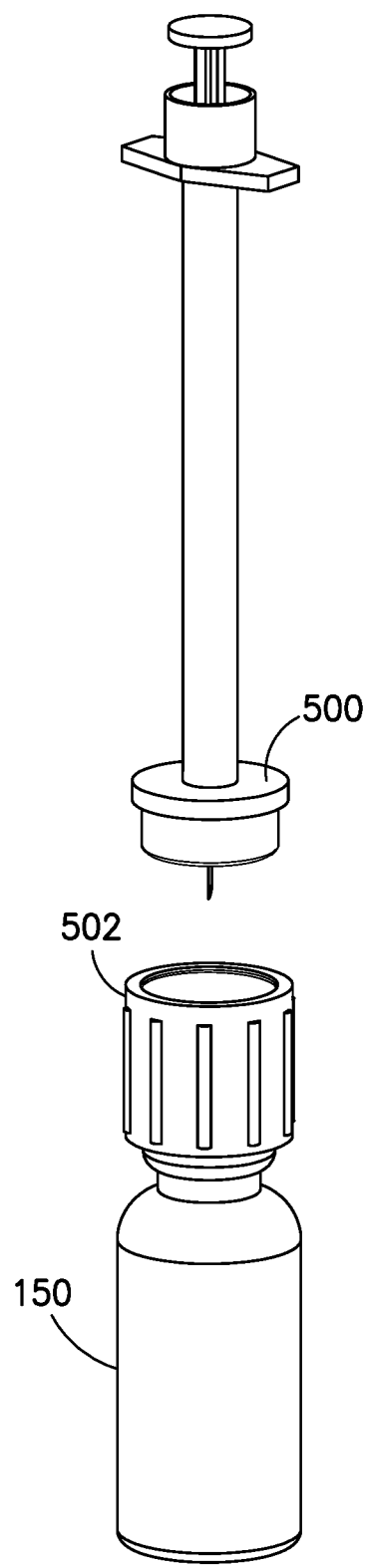

In operation, as shown in FIGS. 18-20, after removing the peel tab 504, the user distally presses the syringe 100 toward the medicament vial 150 and engages the vial stopper holder 160 with the distal end of the vial adapter 502 to enshroud or cover the perimeter of the vial stopper holder 160. As the vial adapter 502 enshrouds the vial stopper holder 160, the vial adapter 502 also aids central axial alignment of the needle 140 and the medicament vial 150.

Subsequently, with continued distal pressing, the user causes the substantially flat distal surface of the needle adapter 500 to register against and align flush with the vial stopper holder 160 to ensure that a tip of the needle 140 is properly inserted into the vial to aspirate the medicament within the vial. According to one embodiment, an axially central substantially flat portion of the needle adapter 500 (surrounding the needle 140) also aligns flush with the septum portion 162 of the vial stopper 165.

After aspirating the desired amount of medicament into the syringe barrel 102, the user withdraws the syringe 100 (along with needle adapter 500), as shown in FIG. 20, thereby readying the syringe 100 for injection. Preferably, the force required to overcome the friction fit between the needle adapter 500 and the vial adapter 502 is greater than the force required to remove the vial adapter 502 from the medicament vial 150. To aid this preference, the vial adapter 502 may have one or more internal ribs 506 (see FIG. 17) that provide added stiffness to the vial adapter 502, and may provide additional compression and/or friction to the fit between the vial adapter 502 and the medicament vial 150.

If, however, the vial adapter 502 comes off the medicament vial 150 with the needle adapter 500, the user can simply remove the vial adapter 502 from the needle adapter 500 prior to injection.

Figure 21:
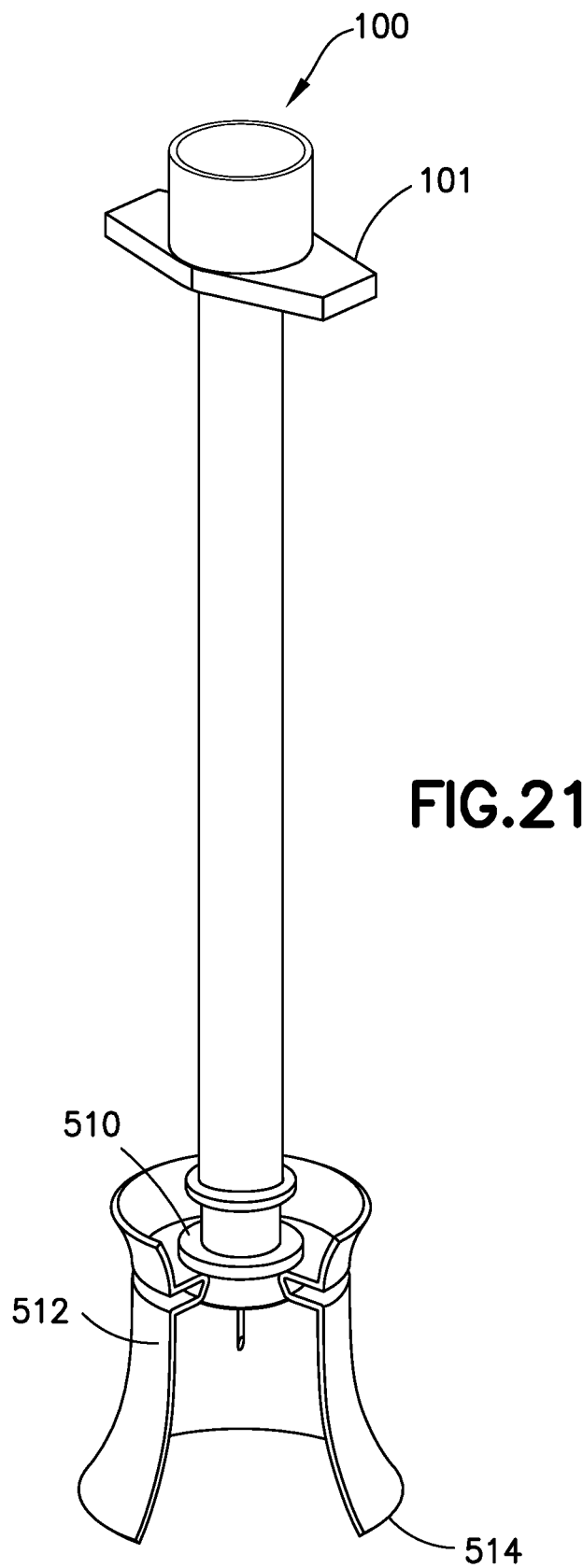
FIG. 21 is an elevational view of a syringe in accordance with another exemplary embodiment of the present invention.
Figure 22:
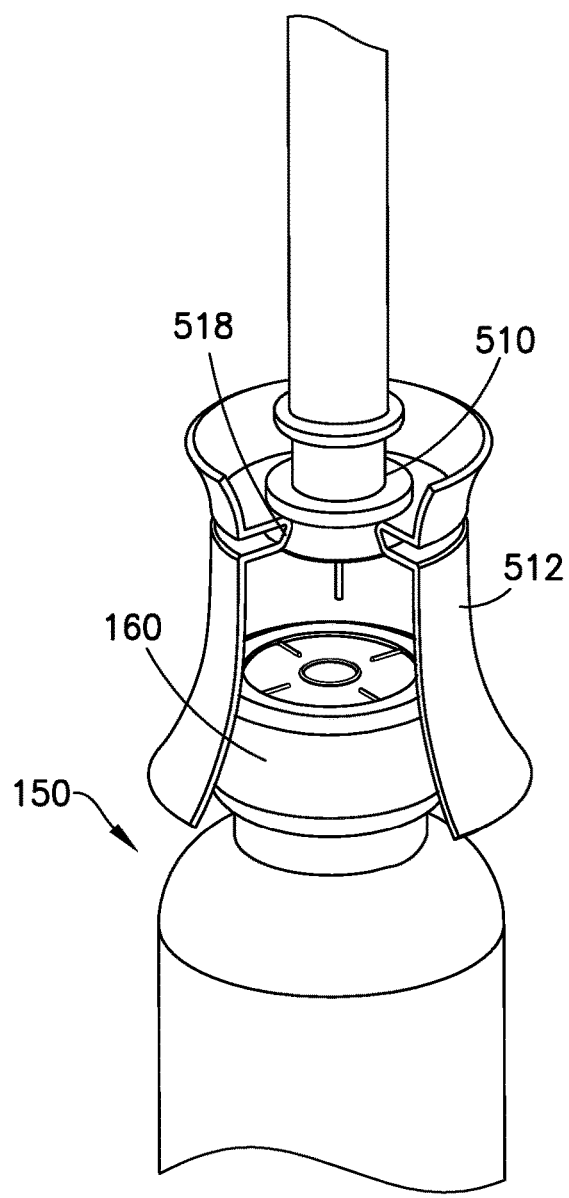
Figure 23:
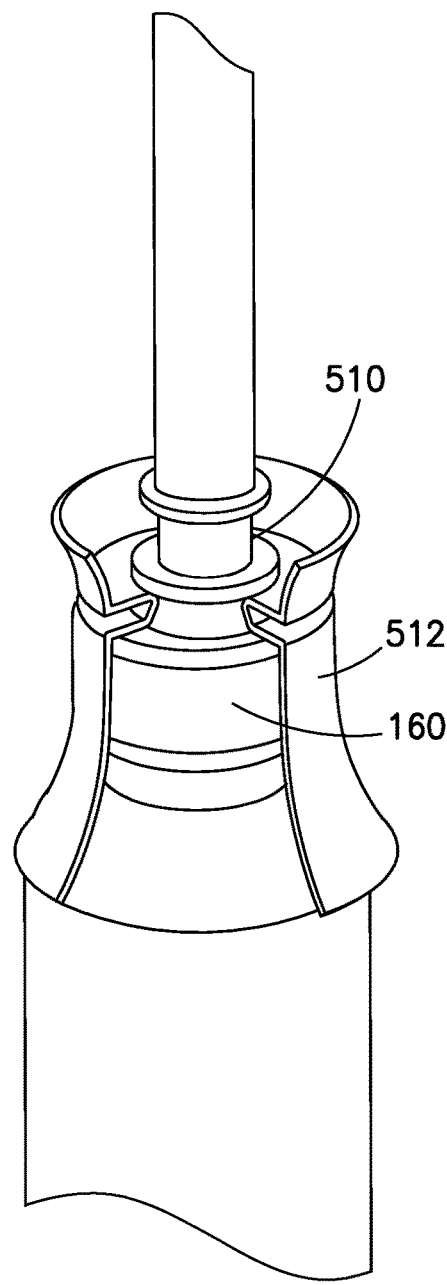
Figure 27:
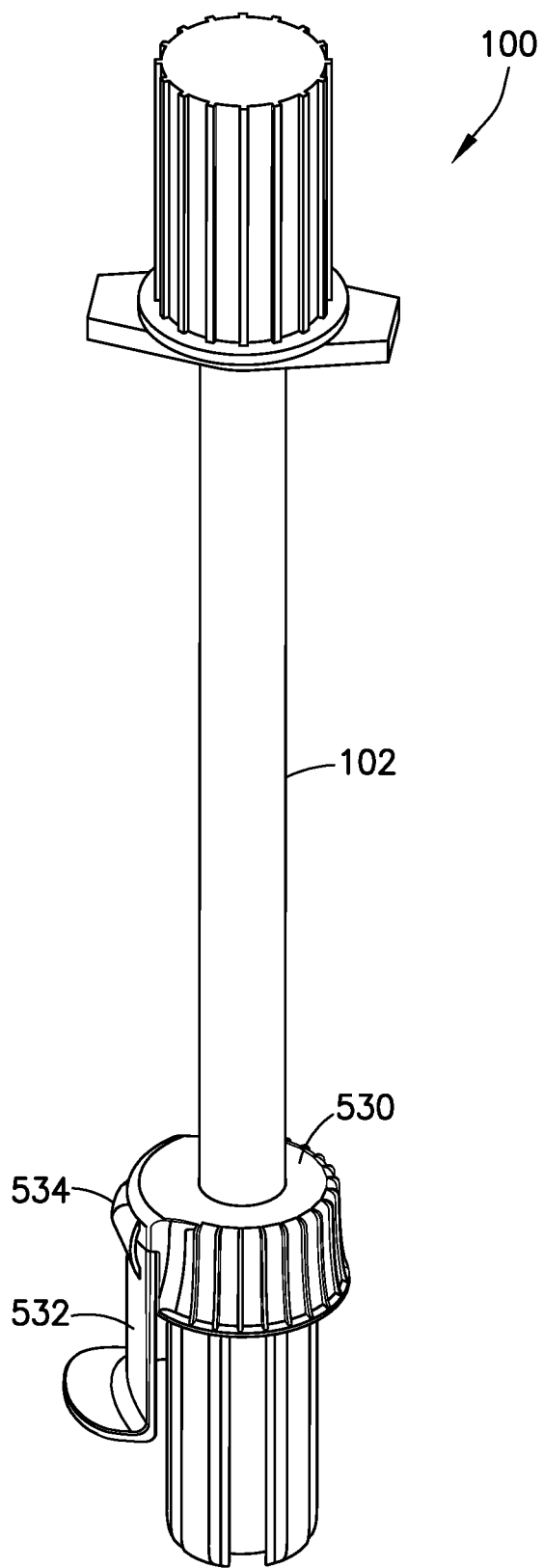
FIGS. 27 and 28 are elevational and partial cross-sectional views of a syringe in accordance with another exemplary embodiment of the present invention.
Figure 29:
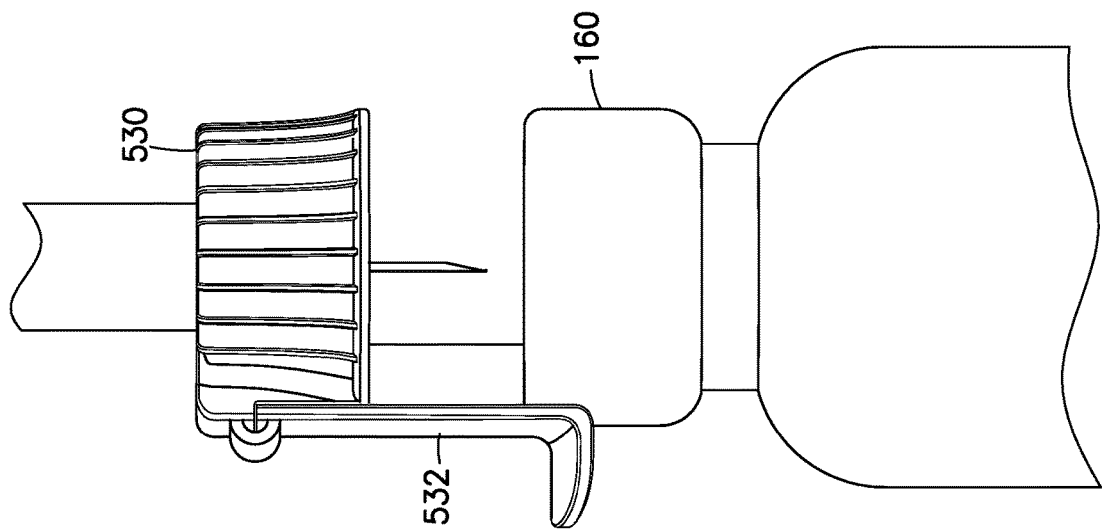
FIGS. 29-31 are partial elevational and cross-sectional views illustrating operation of the syringe of FIG. 27.
Figure 28:
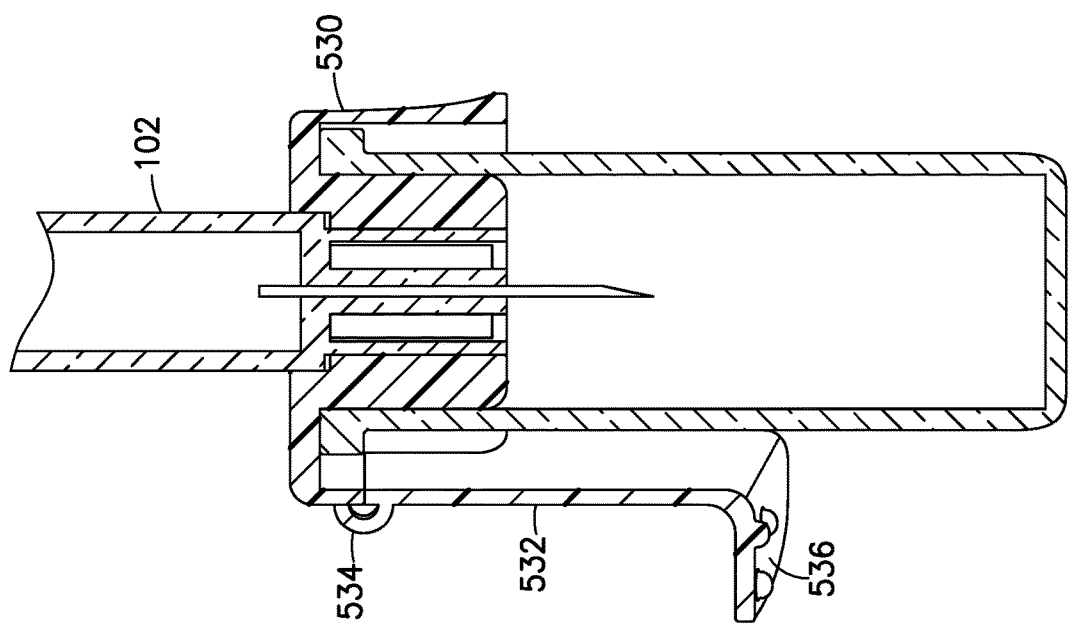

FIG. 21 is an elevational view of a syringe 100 in accordance with another exemplary embodiment of the present invention, and FIGS. 22-24 illustrate interaction of the syringe 100 with the medicament vial 150. As shown in FIG. 21, the needle adapter 510 is disposed at the distal-most end of the syringe body 101, and is initially connected to the vial adapter 512. According to one embodiment, the vial adapter 512 includes a flared distal end 514 with a cutaway, and only partially surrounds the needle adapter 510. The flared distal end 514 is configured to receive the medicament vial 150 and center the vial 150 to aid the central axial alignment of the needle 140 and the vial 150.

As best shown in FIGS. 22 and 24, the needle adapter 510 and the vial adapter 512 have corresponding and mating dovetail shapes 516 and 518 configured to removably connect the needle adapter 510 and the vial adapter 512. The cutaway provides flexibility to the vial adapter 512 for connecting with the vial 150 and disconnecting the needle adapter 510 from the vial adapter 512.

In operation, as shown in FIGS. 22-24, the user distally presses the syringe 100 toward the medicament vial 150 and engages the vial stopper holder 160 with the distal end of the vial adapter 512 to enshroud or cover a majority of the perimeter of the vial stopper holder 160. As the vial adapter 512 partially the vial stopper holder 160, the vial adapter 512 centers the vial 150 and aids central axial alignment of the needle 140 and the medicament vial 150.

With continued distal pressing, the user causes the substantially flat distal (distal most) surface of the needle adapter 510 to register against and align flush with the vial stopper 165 to ensure that a tip of the needle 140 is properly inserted into the vial to aspirate the medicament within the vial (FIG. 23).

After aspirating the desired amount of medicament into the syringe barrel 102, the user withdraws the syringe 100 (along with needle adapter 510), as shown in FIG. 24, thereby readying the syringe 100 for injection. Preferably, the force required to overcome the friction fit between the needle adapter 510 and the vial adapter 512 is greater than the force required to remove the vial adapter 5102 from the medicament vial 150. If, however, the vial adapter 512 comes off the medicament vial 150 with the needle adapter 510, the user can simply remove the vial adapter 512 from the needle adapter 510 prior to injection.

As shown in FIGS. 25 and 26, in accordance with another exemplary embodiment of the present invention, the needle adapter 520 and the vial adapter 522 are initially removably connected with each other. The vial adapter or sleeve 522 has a needle cover 524 frangibly connected thereto, and has cutouts 526 in the sides of the vial adapter 522. According to one embodiment, the needle cover 524 and the vial adapter 522 are integrally formed as a unitary construction with breakaway sprues 528. The cutouts may provide increased flexibility in the sides of the vial adapter in comparison to the sides of the previously described vial adapter 502.

In operation, the user twists the needle cover 524 relative to the vial adapter 522 to break the sprues 528 and remove the needle cover 524. In other aspects, the operation of the needle adapter 520 and the vial adapter 522 are substantially similar to the operation of the previously described needle adapter 500 and the vial adapter 502, and further description is omitted for brevity.

In the embodiment shown in FIGS. 27-31, the vial adapter 532 is hingedly connected to the needle adapter 530, preferably by a bi-stable hinge 534. In addition, according to one embodiment, the vial adapter 532 includes a finger grip 536 configured to aid user manipulation of the vial adapter 532. Preferably, the finger grip 536 includes raised gripping features, such as bumps. In operation, subsequent to removal of the needle cover 536, the user distally presses the syringe 100 toward the medicament vial 150 and engages the vial stopper holder 160 with the vial adapter 532 to center the vial 150 and aid central axial alignment of the needle 140 and the medicament vial 150.

Figure 30:
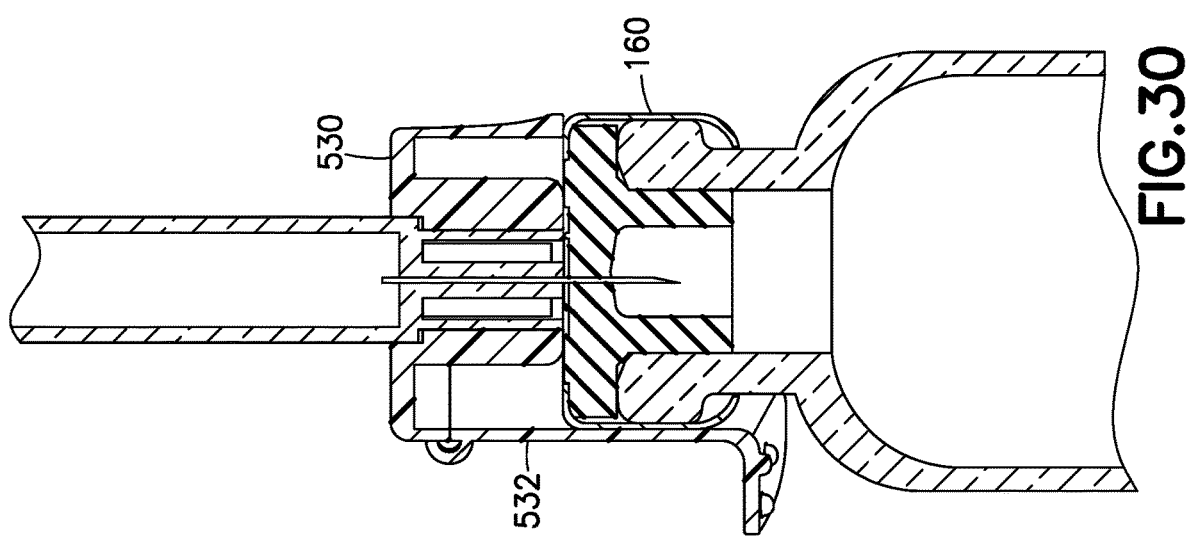

With continued distal pressing, the user causes the substantially flat distal (distal most) surface of the needle adapter 530 to register against and align flush with the vial stopper holder 160 to ensure that a tip of the needle 140 is properly inserted into the vial to aspirate the medicament within the vial (FIG. 30). According to one embodiment, an axially central substantially flat portion of the needle adapter 530 (surrounding the needle 140) also aligns flush with the septum portion 162 of the vial stopper 165.

Figure 31:
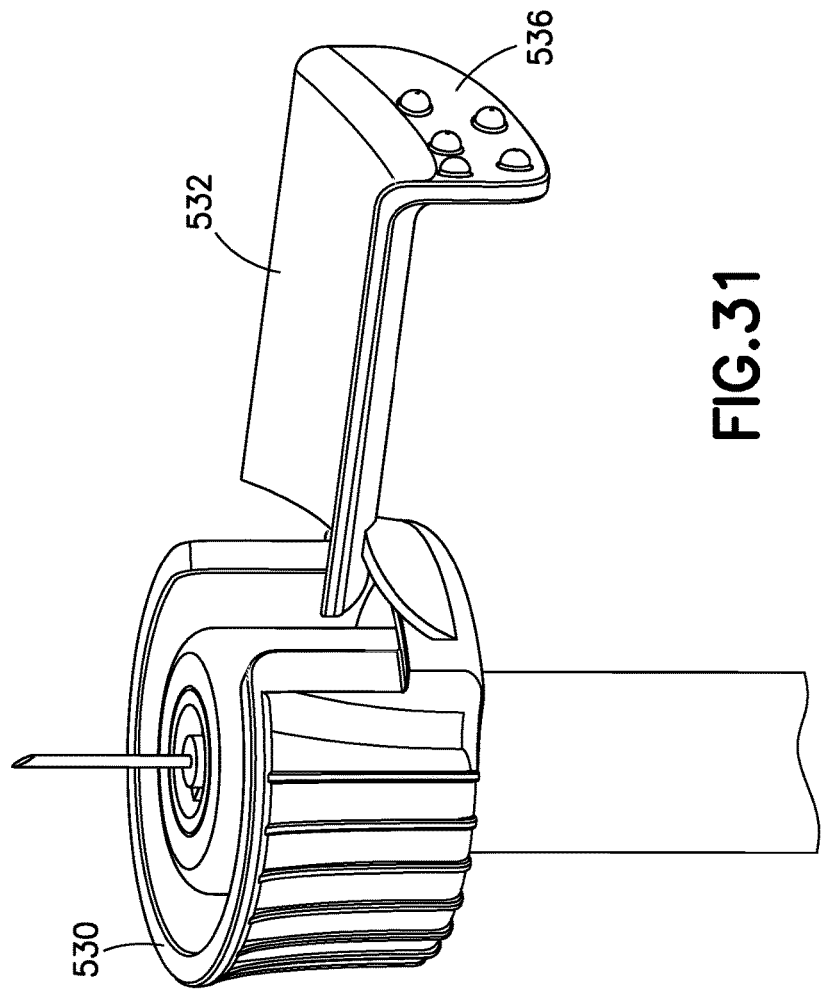

After aspirating the desired amount of medicament into the syringe barrel 102, the user withdraws the syringe 100 (along with needle adapter 530 and the vial adapter 532). Subsequently, the user flips up the vial adapter 532 away from the needle adapter 530, thereby readying the syringe 100 for injection, as shown in FIG. 31.

Figure 32:
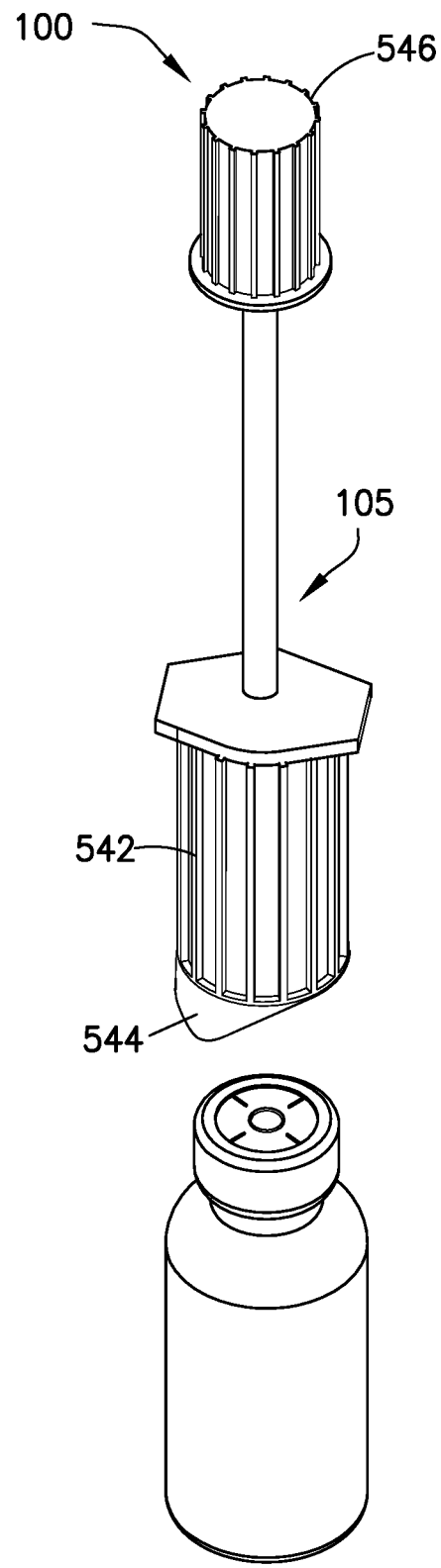
FIGS. 32-34 are elevational a partial cross-sectional views of a syringe in accordance with another exemplary embodiment of the present invention.
Figure 33:
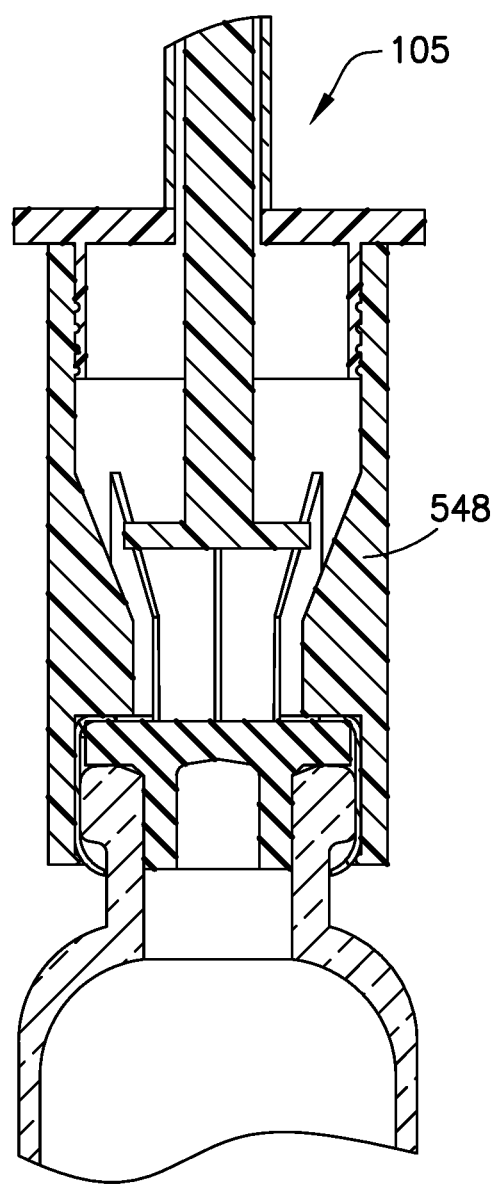
Figure 34:
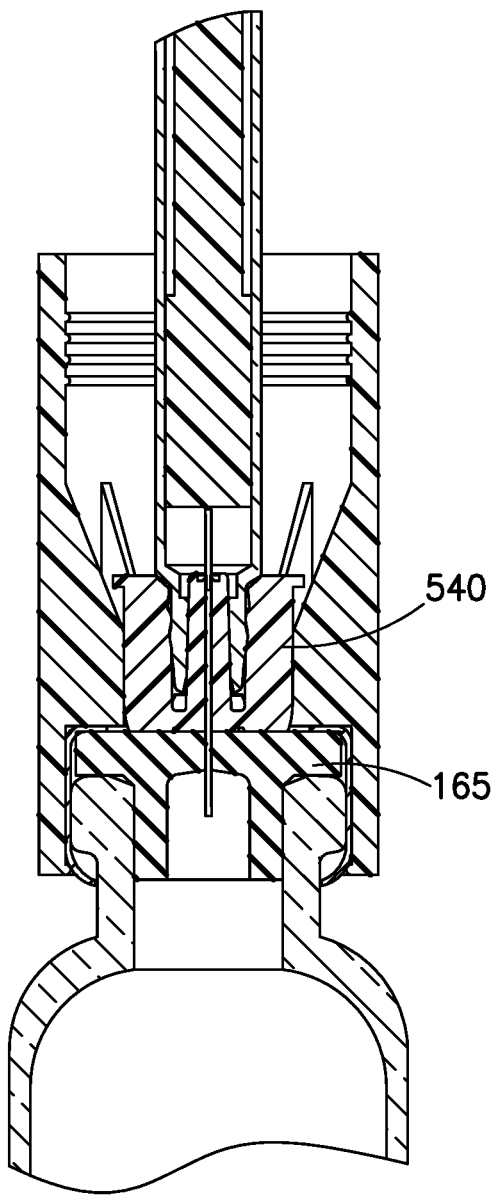

FIGS. 32-34 are elevational a partial cross-sectional views of a syringe 100 in accordance with another exemplary embodiment of the present invention. In this embodiment, as shown in FIG. 32, the vial adapter or sleeve 542 is initially mounted to a plunger end 105 of the syringe 100 at a first end of the vial adapter 542, and is covered by a sterile peel tab 544 at a second, opposite end of the vial adapter 542. The needle 140 and the needle adapter 540 are preferably covered by a removable needle cover 546.

In one mode of operation, illustrated in FIG. 33, after the user removes the peel tab 544, the user proximally presses the syringe 100 toward the medicament vial 150 and engages the vial stopper holder 160 with the second end of the vial adapter 542 to enshroud or cover a majority of the perimeter of the vial stopper holder 160. As shown in FIG. 33, according to one embodiment, the vial adapter 542 includes a plurality of internal axial ribs 548 that are configured to provide clearance for the plunger 120, engage and register the ribs 548 against the vial stopper holder 160, and aid central axial alignment of the needle 140 and the vial 150 (as shown in FIG. 34).

In this mode of operation, the user subsequently removes the plunger end 105 of the syringe 100 from the vial adapter 542, reverses the syringe 100, removes the needle cover 546, and distally inserts the needle adapter 540 into the vial adapter. In conjunction with the axial ribs 548, the needle adapter 540 facilitates a flush alignment of the substantially flat distal (distal-most) surface of needle adapter 540 with the vial stopper 165 to ensure that a tip of the needle 140 is properly inserted into the vial 150 to aspirate the medicament within the vial 150, as shown in FIG. 34.

After aspirating the desired amount of medicament into the syringe barrel 102, the user withdraws the syringe 100 (along with needle adapter 540), thereby readying the syringe 100 for injection. Preferably, the force required to overcome the friction fit between the needle adapter 540 and the vial adapter 542 is greater than the force required to remove the vial adapter 542 from the medicament vial 150. If, however, the vial adapter 542 comes off the medicament vial 150 with the needle adapter 540, the user can simply remove the vial adapter 542 from the needle adapter 540 prior to injection.

According to another mode of operation, rather than maintaining the vial adapter 542 on the plunger end 105 of the syringe 100 to engage the vial adapter 542 with the vial stopper holder 160, the user can remove the vial adapter 542 from the syringe 100 prior to engaging the vial adapter 542 with the vial stopper holder 160.

FIG. 35 is and elevational views of a syringe 100 in accordance with another exemplary embodiment of the present invention, and FIGS. 36-39 are partial elevational views illustrating filling of the syringe 100. The syringe 100, in addition to a needle adapter 550, includes a sliding vial adapter 552.

The vial adapter 552 slides relative to the needle adapter 550 along an axis substantially parallel to the longitudinal axis of the needle 140. Preferably, the vial adapter 552 includes a handle portion 557 fixedly connected at a first end to a sliding guide portion 558, configured to slide along the syringe barrel 102, and fixedly connected at a second end to a clip portion 559 configured to laterally clip onto a neck portion 153 of the vial 150. According to one embodiment, the clip portion 559 includes a C-shaped clip 559 configured to flexibly clip onto the neck portion 153 and surround a majority of the neck portion 153.

In an alternative embodiment, the clip portion 559 is fixedly connected directly to the sliding guide portion 558.

Figure 37:
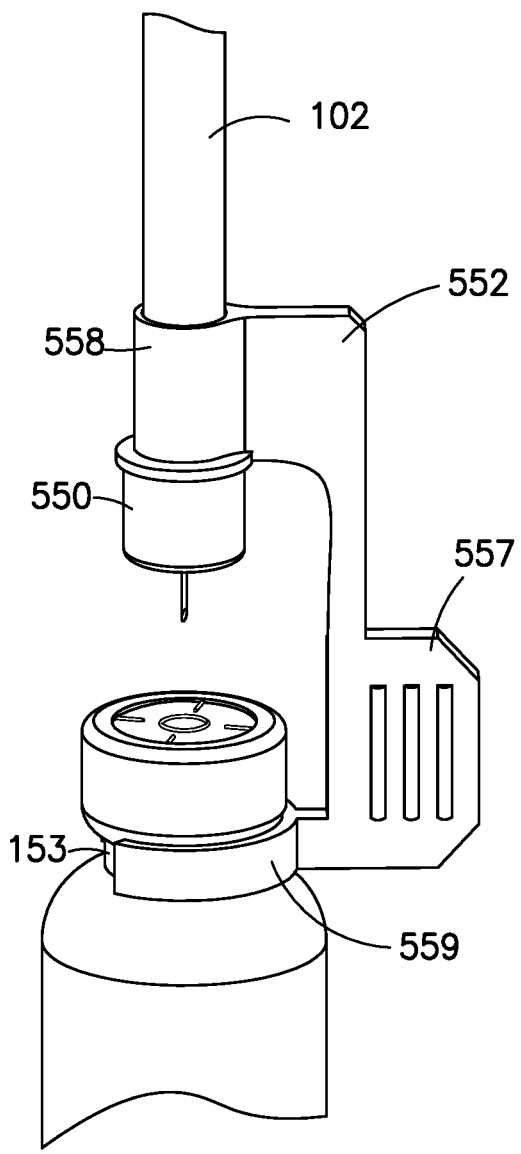
Figure 38:
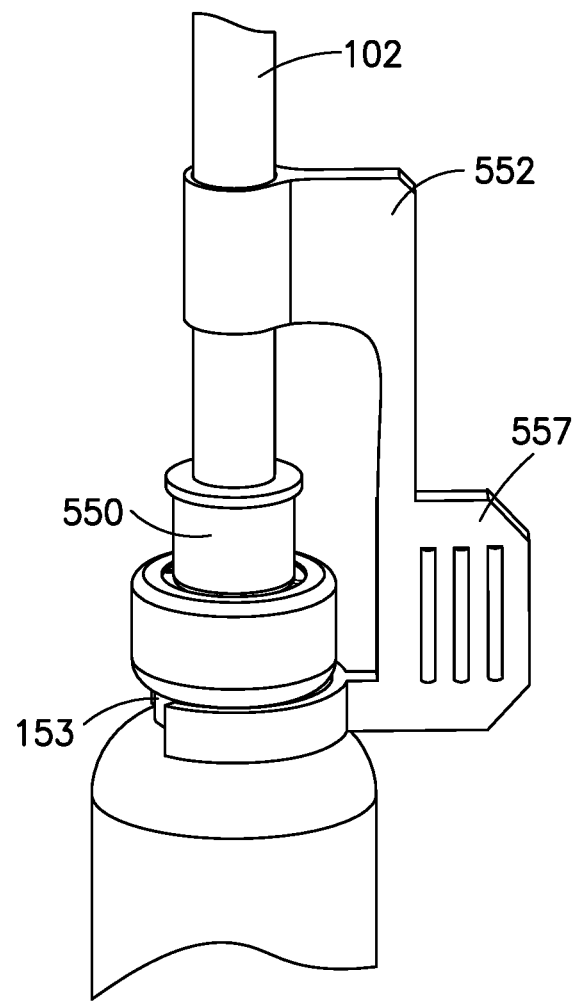
Figure 39:
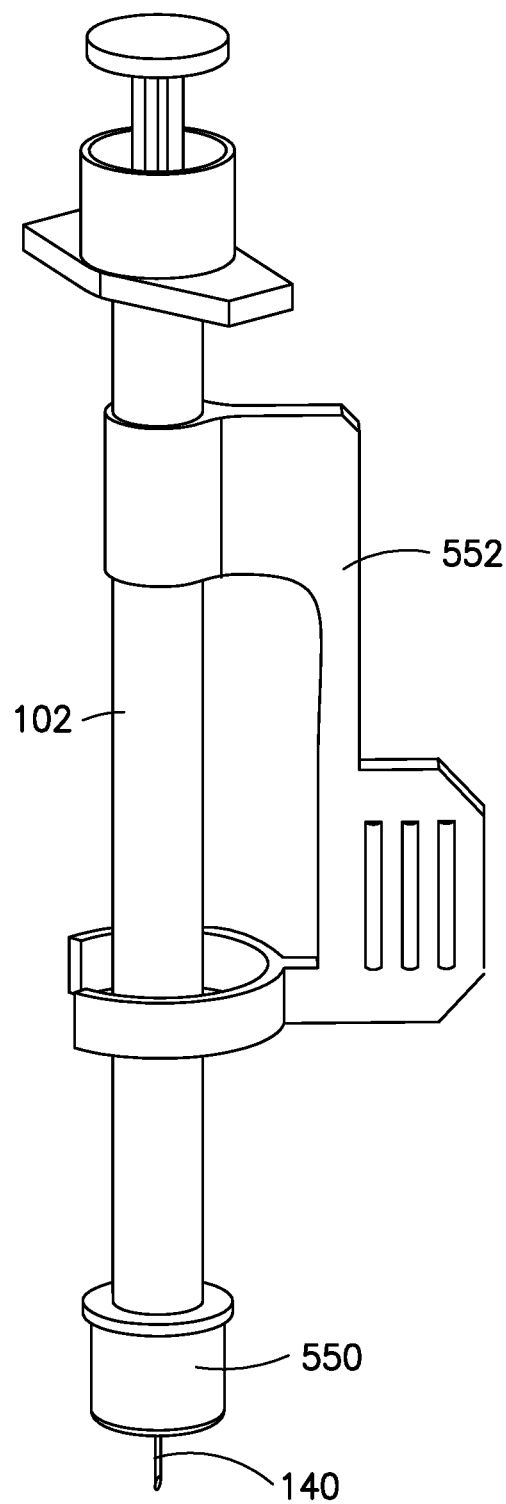

In operation, as shown in FIGS. 36-39, after removing the needle cover 554 and the plunger cover 556, the user slides the syringe barrel 102 proximally relative to the vial adapter 552 until there is sufficient clearance that the clip portion 559 can engage the neck portion 153 of the vial 150 without the needle 140 contacting the vial 150. For example, the user can slide the syringe barrel 102 until the needle adapter 550 contacts the sliding guide portion 558 (FIG. 37).

Then, the user clips the clip portion 559 onto the neck portion, centering the medicament vial 150 and aiding the central axial alignment of the needle 140 and the vial 150 (FIG. 37). Subsequently, the user slides the syringe barrel 102 distally relative to the vial adapter 552 and the vial 150, until the substantially flat distal (distal-most) surface of the needle adapter 550 aligns flush with the vial stopper 165 to ensure that the tip of the needle 140 is properly inserted into the vial 150 to aspirate the medicament within the vial 150.

After aspirating the desired amount of medicament into the syringe barrel 102, the user withdraws the syringe barrel 102 proximally (along with needle adapter 550) to a position in which the needle 140 clears the vial, such as the position illustrated in FIG. 37. Subsequently, the user unclips the clip portion 559 from the neck 153 and slides the vial adapter 552 proximally relative to the syringe barrel 102 to expose the needle 140 (FIG. 39), thereby readying the syringe 100 for injection.

Referring back to FIG. 35, in its initial state, the syringe 100 includes a removable needle cover 554 and optionally includes a removable plunger cover 556.

Figure 40:
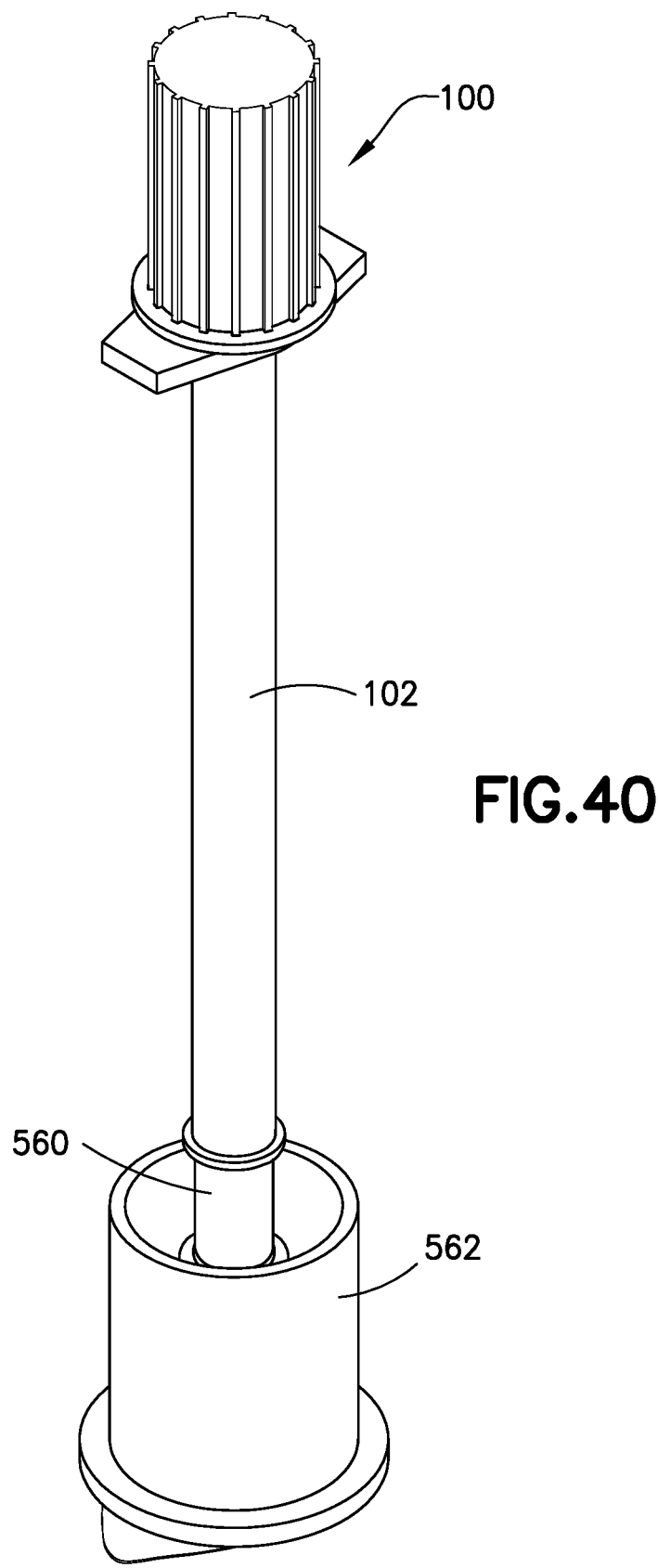
FIG. 40 is an elevational view of a of a syringe in accordance with another exemplary embodiment of the present invention.
Figure 41:
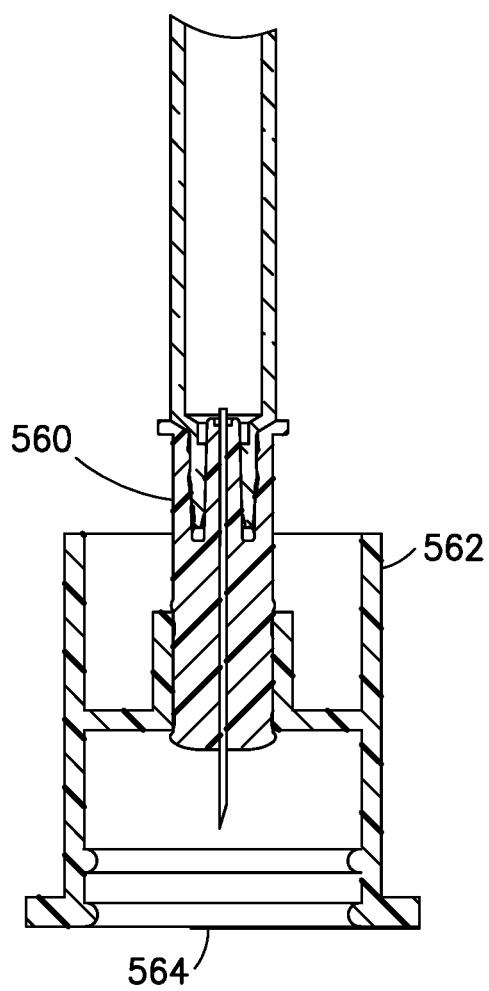
Figure 42:
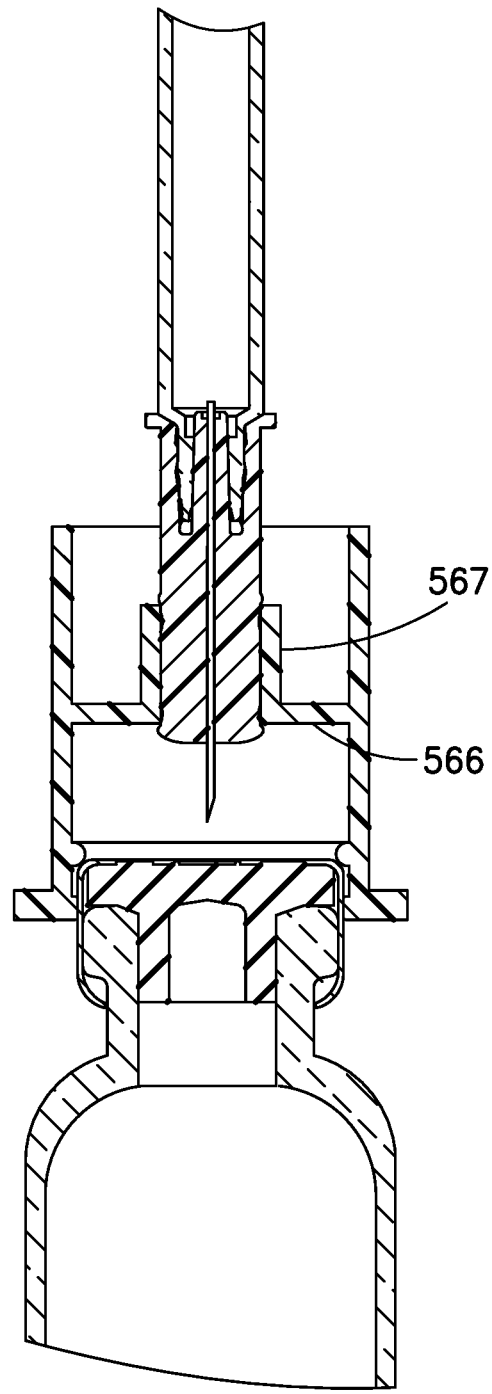

FIG. 40 is an elevational view of a of a syringe 100 in accordance with another exemplary embodiment of the present invention, and FIGS. 41-44 are partial cross-sectional views of the syringe of FIG. 40 illustrating operation thereof. The syringe 100 includes a needle adapter 560 with substantially flat distal (distal-most) surface, and a vial adapter or sleeve 562 slidably connected to the needle adapter 560 and having a first end configured to removably receive the vial stopper holder 160. Preferably, the first end of the vial adapter 562 is initially covered by a peel tab 564, which, along with the tortuous path slidable connection of the vial adapter 562 with the needle adapter 560, ensures sterility of the needle 140 prior to use.

Preferably, the vial adapter 562 includes an internal radial flange 566 with an axial portion 567 configured to slidably grip the needle adapter 560.

In operation, after removing the peel tab 564, the user engages the vial adapter 562 with the vial stopper holder 160 (FIG. 42) to aid central axial alignment of the needle 140 and the vial 150, preferably, by grasping the vial adapter 562 and pressing it toward the vial 150. The user continues to distally press the vial adapter toward the vial 150 until the substantially flat distal portion of the needle adapter 560 aligns flush with the vial stopper 165, to ensure that the tip of the needle 140 is properly inserted into the vial 150 to aspirate the medicament within the vial 150 (FIG. 43).

After aspiration of the medicament into the syringe barrel 102, the user removes the syringe 100 (including the vial adapter 562 and the needle adapter 560) from the vial 150. According to one embodiment, the syringe is now ready for injection, and the vial adapter 562 will slide proximally relative to the needle adapter 560 as the user inserts the needle 140 into the patient (FIG. 44). Alternatively, the user can manually slide the vial adapter 562 proximally relative to the needle adapter 560 to expose the needle 140 prior to injection (FIG. 44).

Preferably, as shown in FIG. 44, the vial adapter 562 includes one or more internal circumferential ribs 568 configured to aid the connection of the vial adapter 562 with the vial stopper holder 160.

Figure 45:
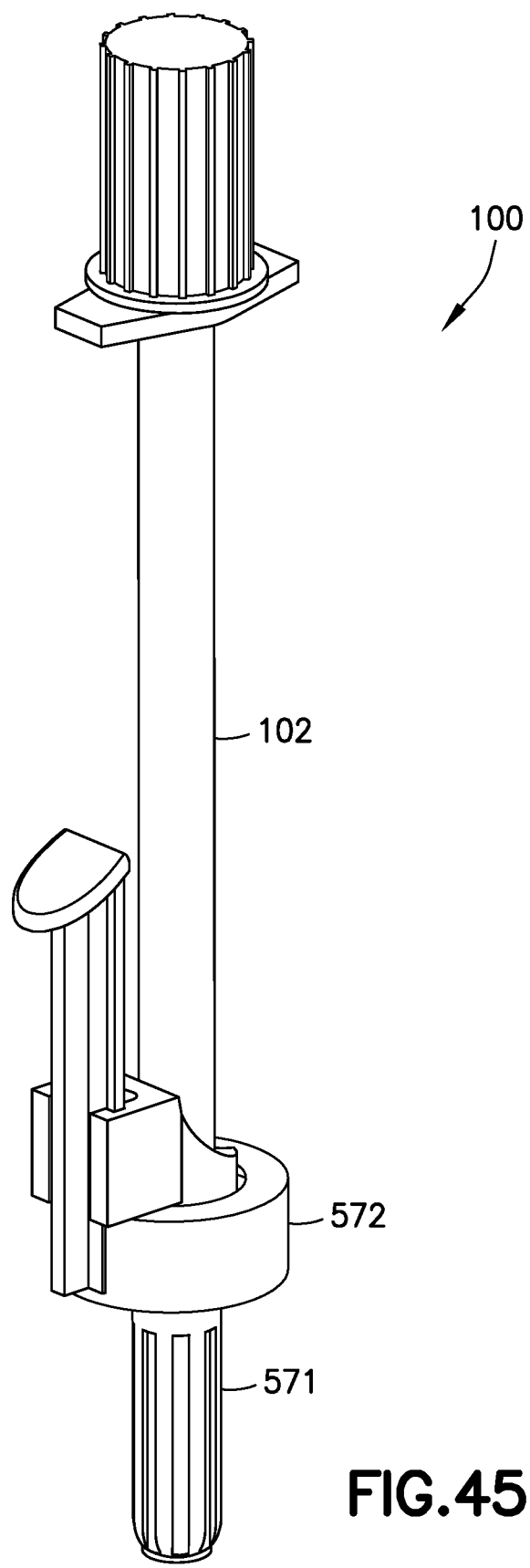
FIG. 45 is an elevational view of a of a syringe in accordance with another exemplary embodiment of the present invention.
Figure 52:
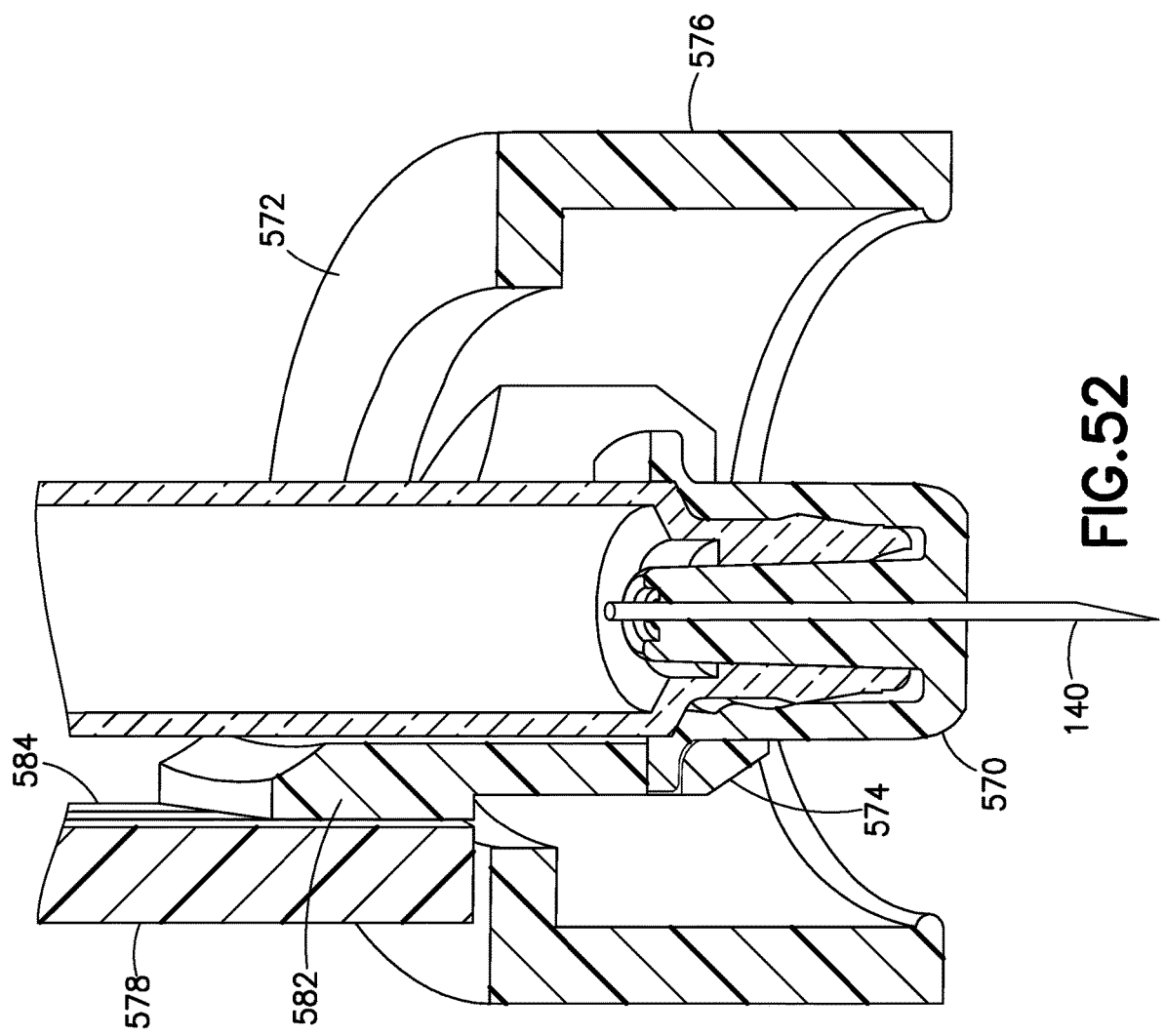
FIG. 52 is a partial cross-sectional view of the syringe of FIG. 45.
Figure 53:
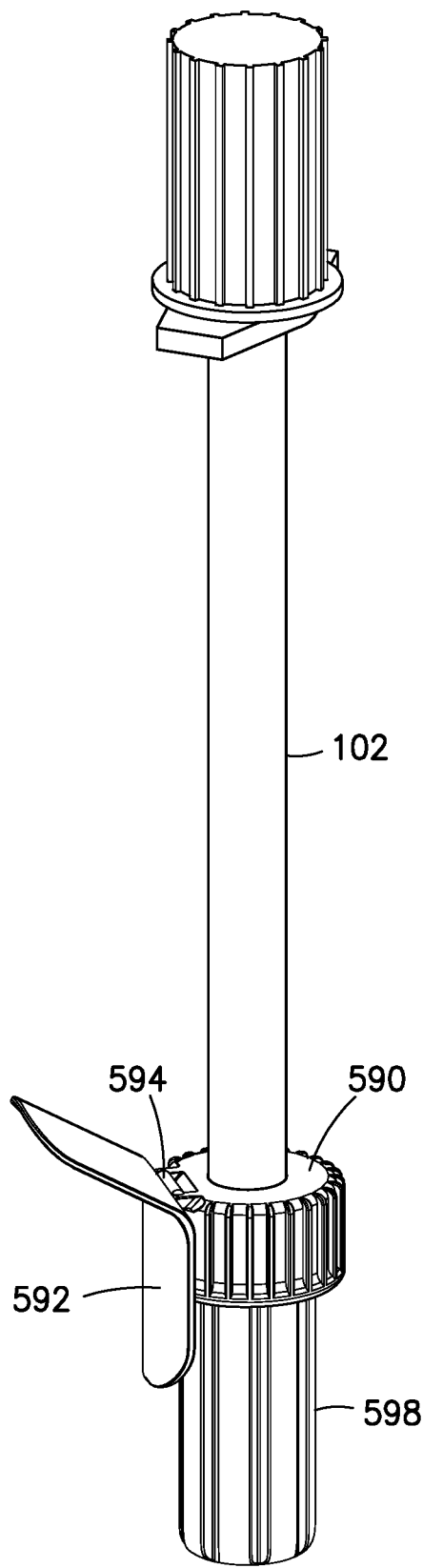
FIG. 53 is an elevational views of a syringe in accordance with another exemplary embodiment of the present invention.

FIG. 45 is an elevational view of a of a syringe 100 in accordance with another exemplary embodiment of the present invention, FIGS. 46-51 are partial elevational views of the syringe 100 of FIG. 45 illustrating operation thereof, and FIG. 52 is a partial cross-sectional view of the syringe 100 of FIG. 45.

Figure 46:
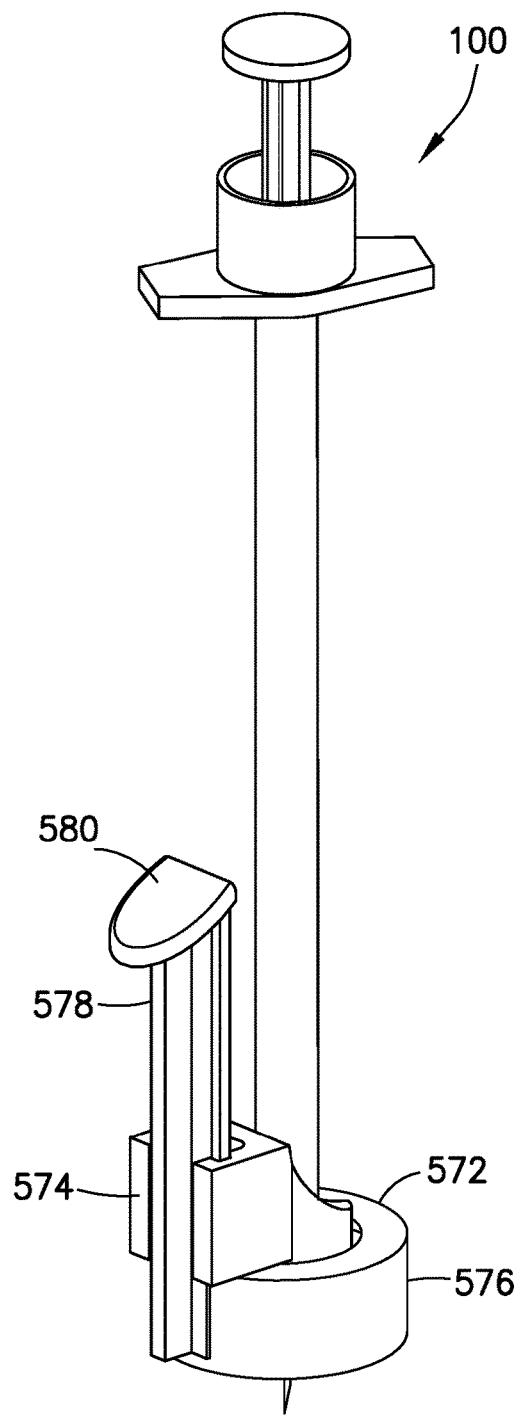
FIGS. 46-51 are partial elevational views of the syringe of FIG. 45 illustrating operation thereof.
Figure 47:
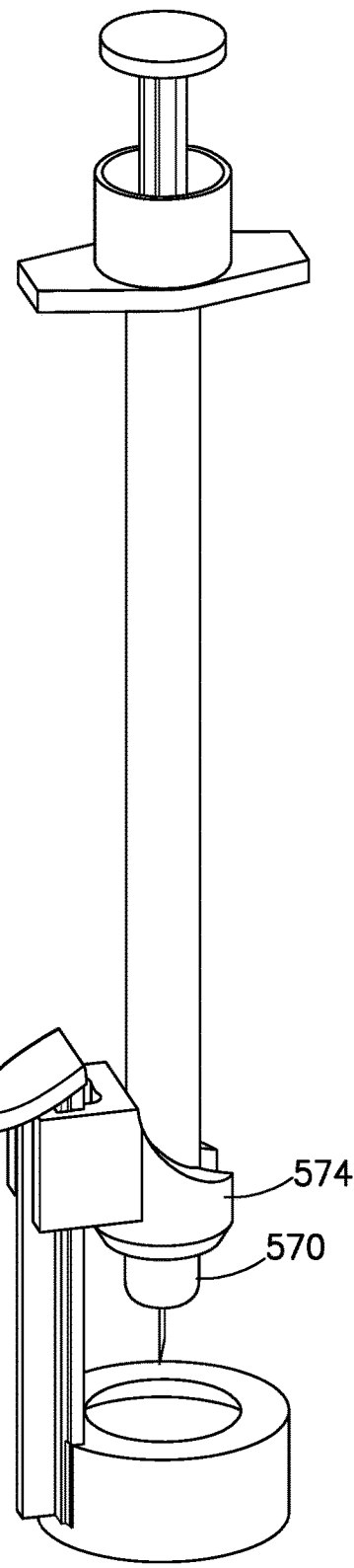

As shown in FIGS. 45-47, the syringe 100 includes a vial adapter 572 configured to slide relative to the needle adapter 570 along an axis substantially parallel to the longitudinal axis of the needle 140. The syringe 100 also includes a guiding member 574 fixedly disposed on the needle adapter 570 (best shown in FIG. 52), and the vial adapter 572 includes a sleeve portion 576 and an extension 578 configured to slidably engage with the guiding member 574. Preferably, the guiding member 574 includes a T-slot and the extension 578 includes a T-shaped member configured to slidably engage the T-slot. According to another embodiment, however, the guiding member 574 includes the T-shaped member and the extension includes the T-slot. Preferably, the extension 578 also includes a finger 580 configured to aid user manipulation of the vial adapter 572.

Figure 49:
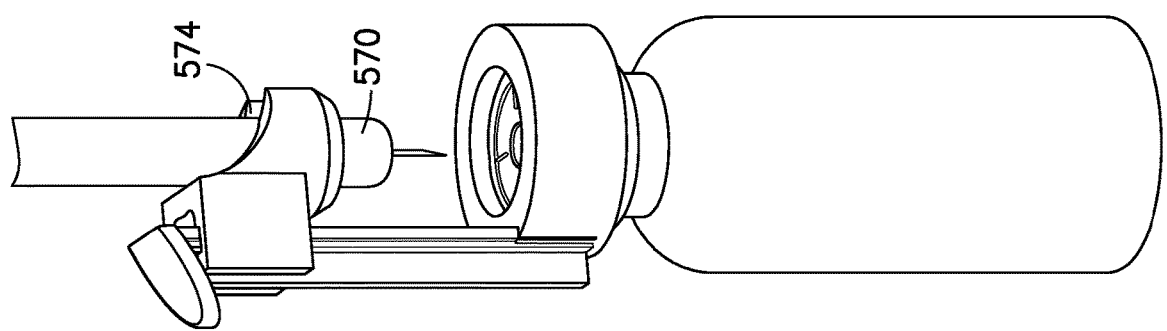
Figure 48:
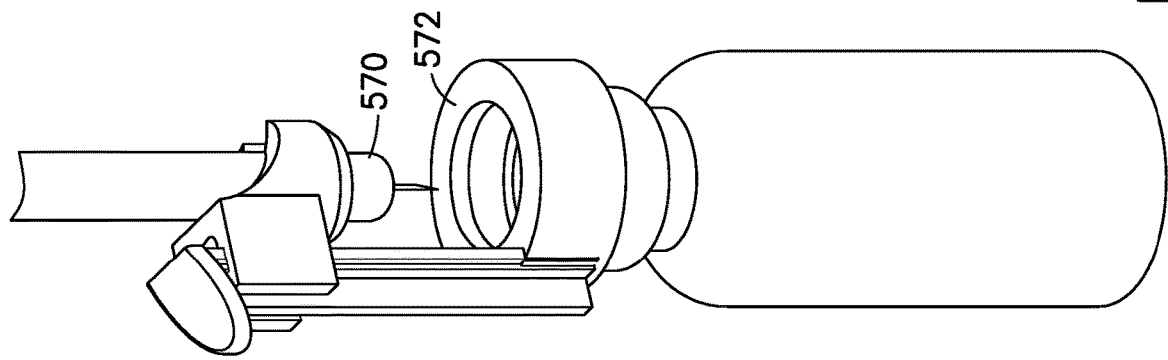
Figure 51:
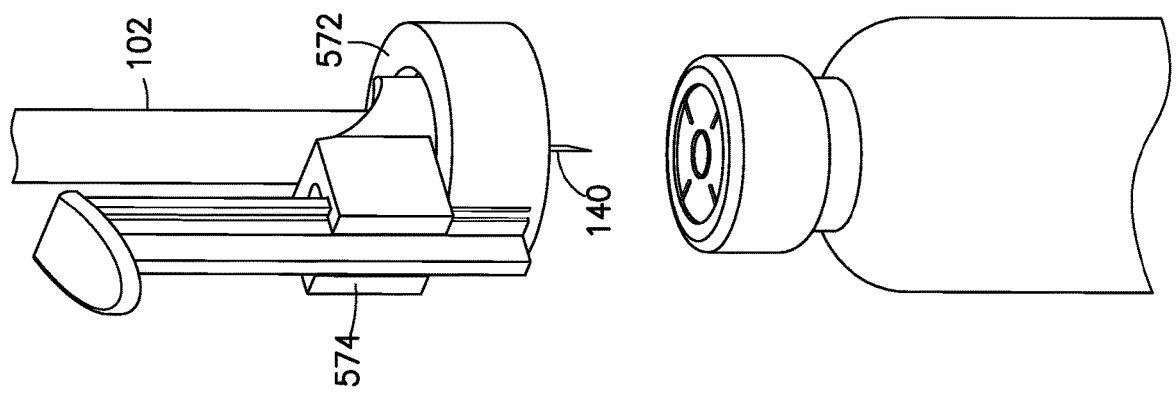
Figure 50:
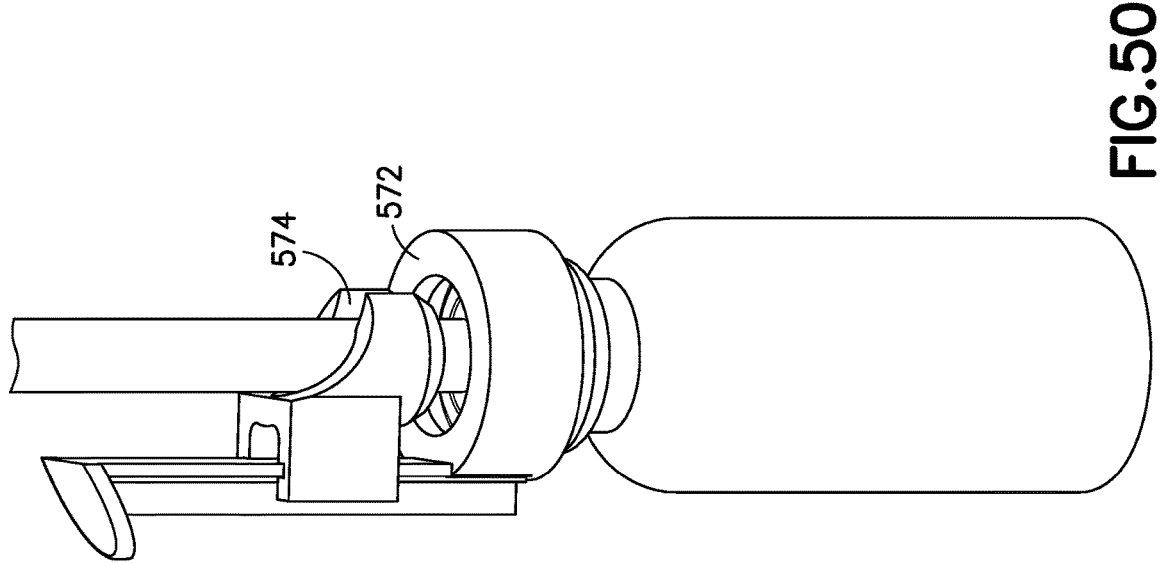

In operation, as shown in FIGS. 46-51, after removal of the needle cover 571 (FIG. 46), the user slides the vial adapter 572 distally relative to the needle adapter 570 to an offset positioning of the vial adapter 572 relative to the needle adapter 570 to provide clearance for the needle 140 (FIG. 47). Then, the user engages the vial adapter 572 with the vial stopper holder 160 (FIG. 48) (preferably by grasping the vial adapter 572), and continues pressing the vial adapter 572 distally toward the vial 150 until the sleeve portion 576 registers flush against the vial stopper holder 160 while preferably maintaining the offset positioning of the vial adapter relative to the needle adapter 570 (FIG. 49). In this position, the vial adapter 572 engages the vial stopper holder 160 to aid central axial alignment of the needle 140 and the vial 150.

Subsequently, the user slides the syringe barrel 102 and the needle adapter 570 distally relative to the vial adapter 572 and the vial 150, to align the substantially flat distal (distal-most) surface of the needle adapter 570 flush with the vial stopper 165 to ensure that the tip of the needle 140 is properly inserted into the vial 150 to aspirate the medicament within the vial 150.

After aspiration of the medicament into the syringe barrel 102, the user removes the syringe 100 (including the needle adapter 570 and the vial adapter 572) from the vial 150, thereby readying the syringe 100 for injection.

According to one mode of operation, the contact of the vial adapter 572 on a patient's skin raises the vial adapter 572 relative to the needle adapter 570 as the needle 140 is inserted into the patient's skin. According to another mode of operation, the user lifts the vial adapter 572 relative to the needle adapter 570 prior to injection.

Similar to the embodiment shown in FIGS. 27-31, in the embodiment of FIGS. 53-56, the vial adapter 592 is hingedly connected to the needle adapter 590 by a hinge 594. According to on embodiment, the hinge 594 is a bi-stable hinge 594. In addition, according to one embodiment, the vial adapter 532 includes a finger grip 596 (best shown in FIG. 56) configured to aid user manipulation of the vial adapter 592. Preferably, the finger grip 596 includes raised gripping features, such as bumps.

Figure 54:
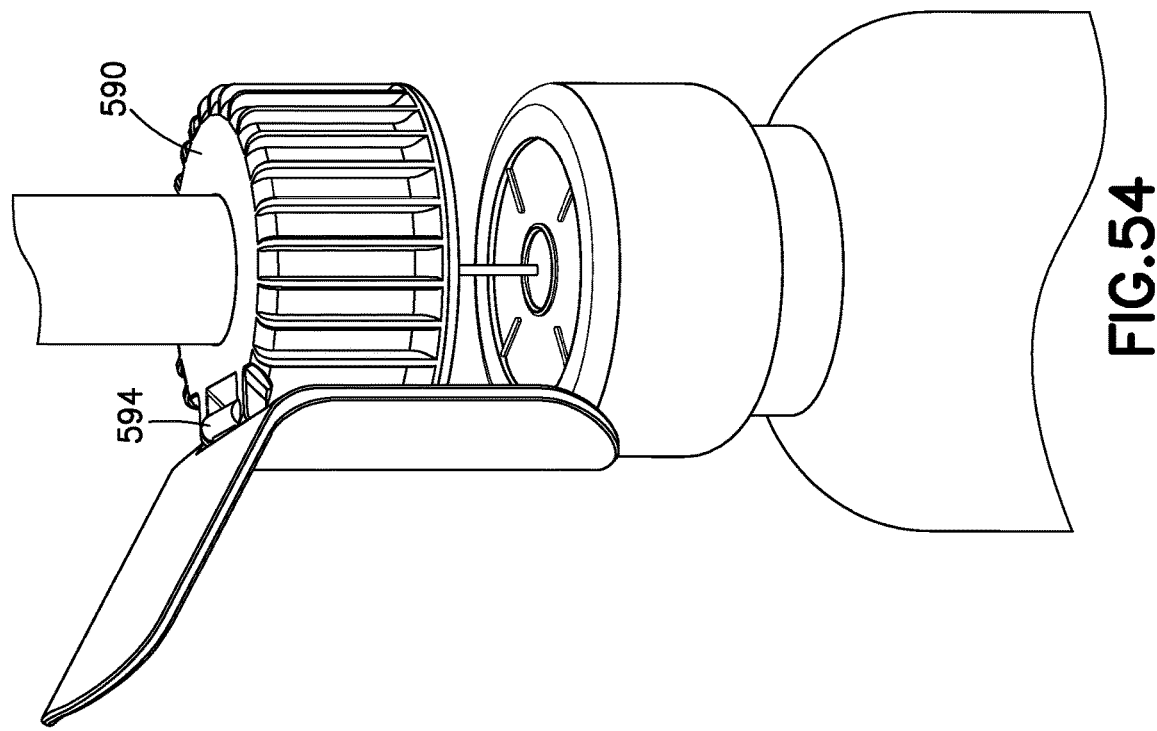

In operation, subsequent to removal of the needle cover 598, the user distally presses the syringe 100 toward the medicament vial 150 and engages the vial stopper holder 160 with the vial adapter 592 to center the vial 150 and aid central axial alignment of the needle 140 and the medicament vial 150 (FIG. 54).

Figure 55:
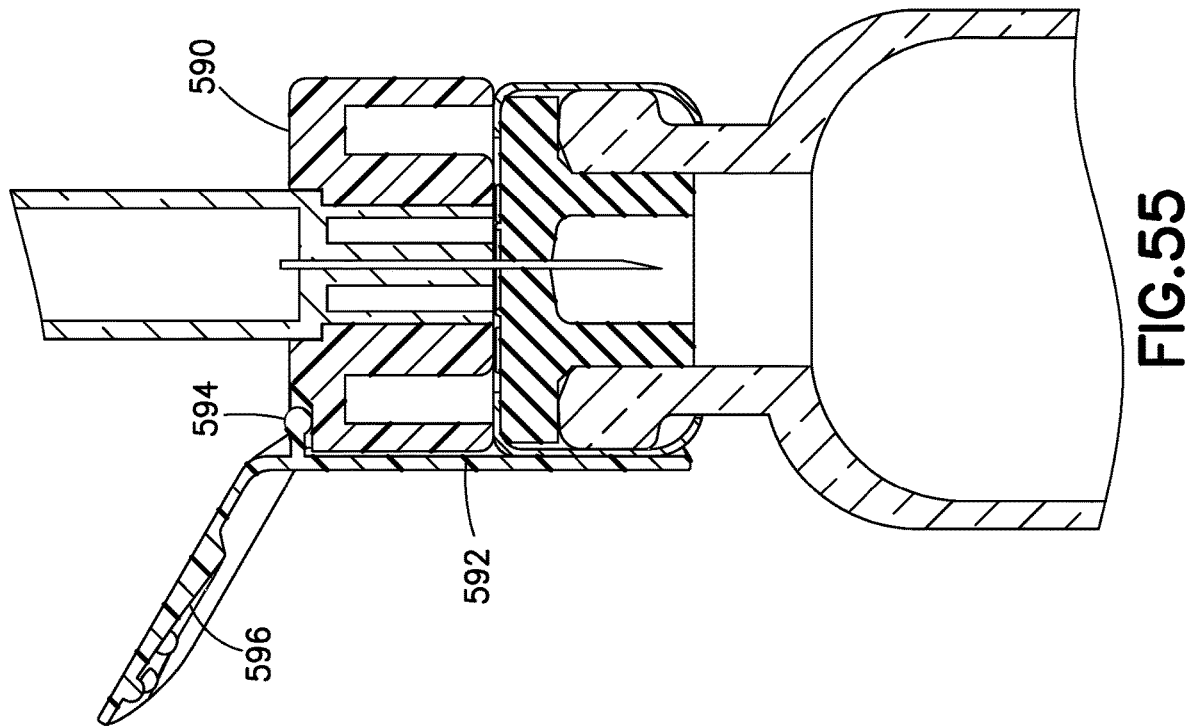
FIGS. 54-56 are partial elevational and cross-sectional views illustrating operation of the syringe of FIG. 53.

With continued distal pressing, the user causes the substantially flat distal (distal most) surface of the needle adapter 590 to register against and align flush with the vial stopper holder 160 to ensure that a tip of the needle 140 is properly inserted into the vial to aspirate the medicament within the vial (FIG. 55). According to one embodiment, an axially central substantially flat portion of the needle adapter 590 (surrounding the needle 140) also aligns flush with the septum portion 162 of the vial stopper 165.

Figure 56:
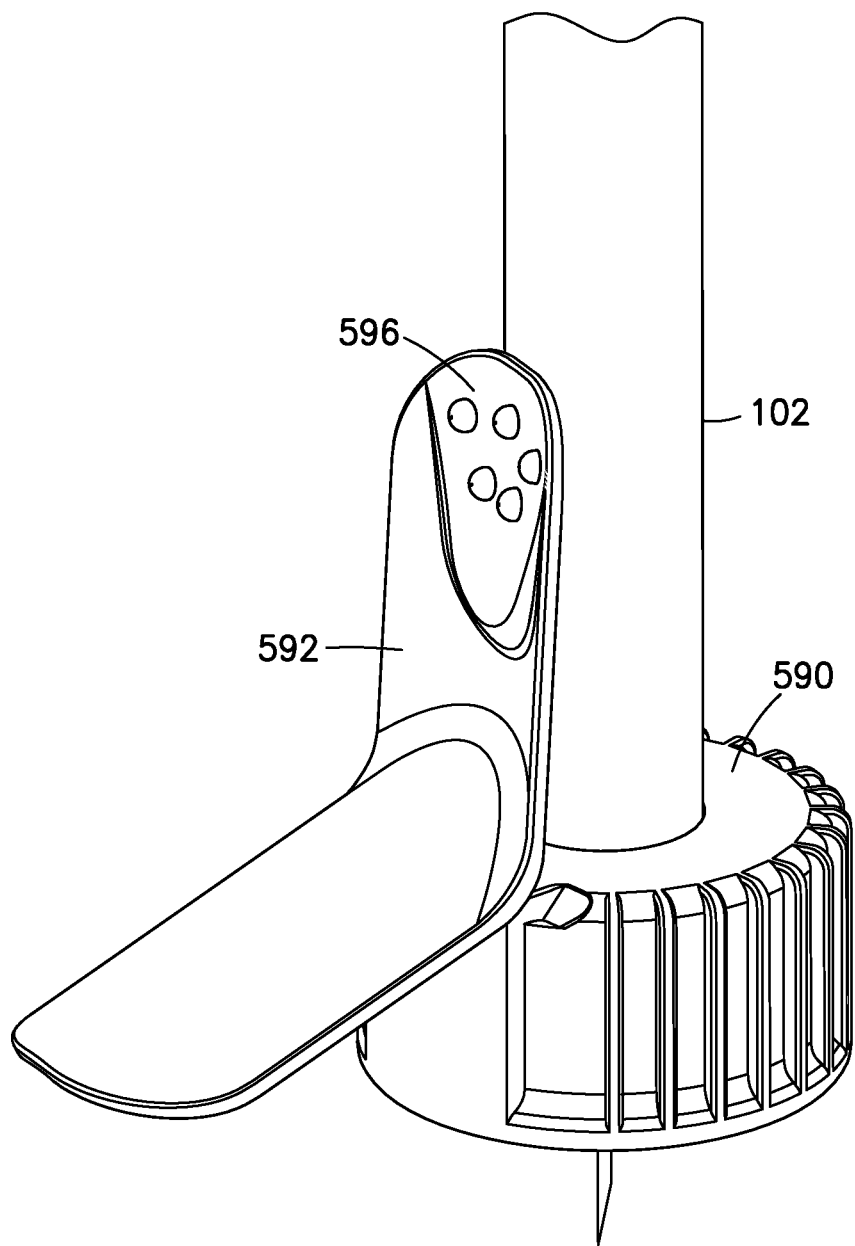

After aspirating the desired amount of medicament into the syringe barrel 102, the user withdraws the syringe 100 (along with needle adapter 530 and the vial adapter 532). Subsequently, the user flips up the vial adapter 592 about the hinge 594, thereby readying the syringe 100 for injection, as shown in FIG. 56.

Figure 57:
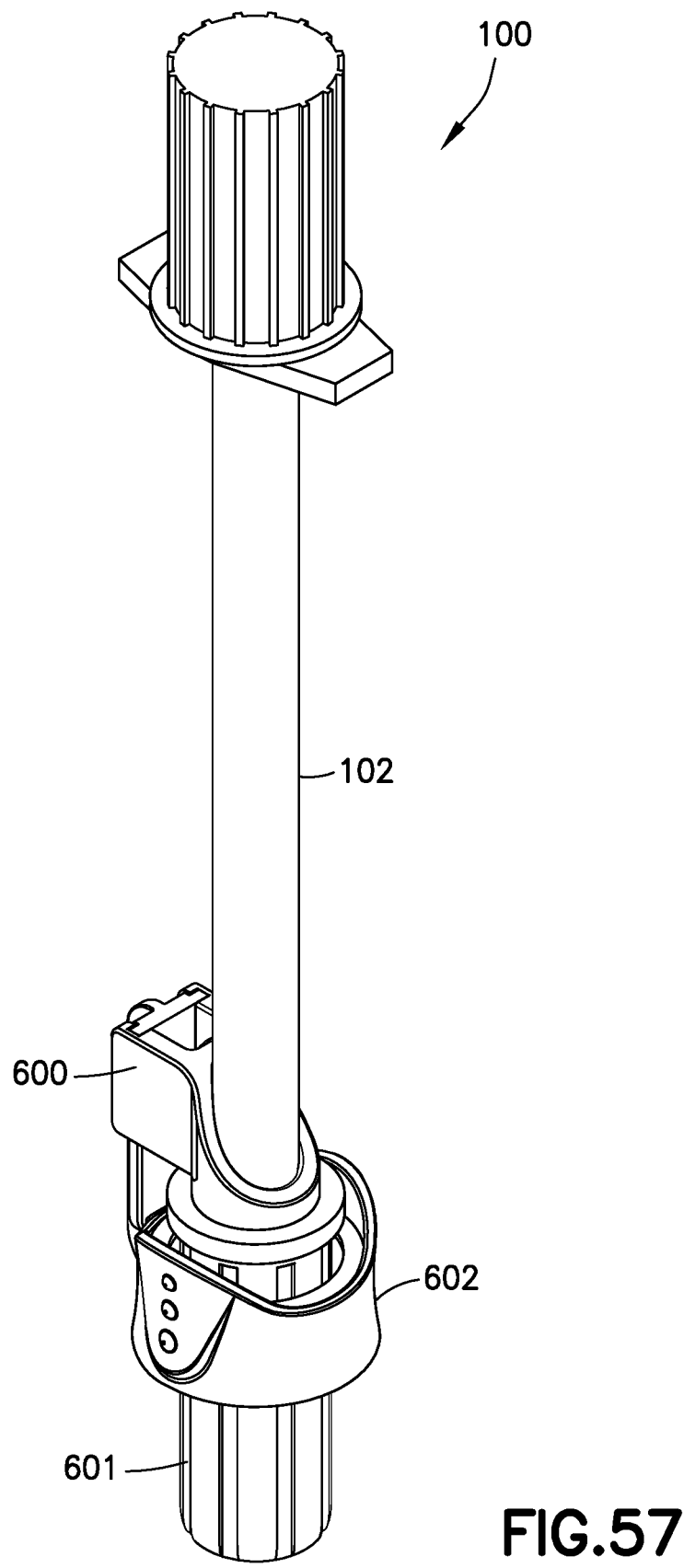
FIG. 57 is an elevational view of a of a syringe in accordance with another exemplary embodiment of the present invention.
Figure 59:
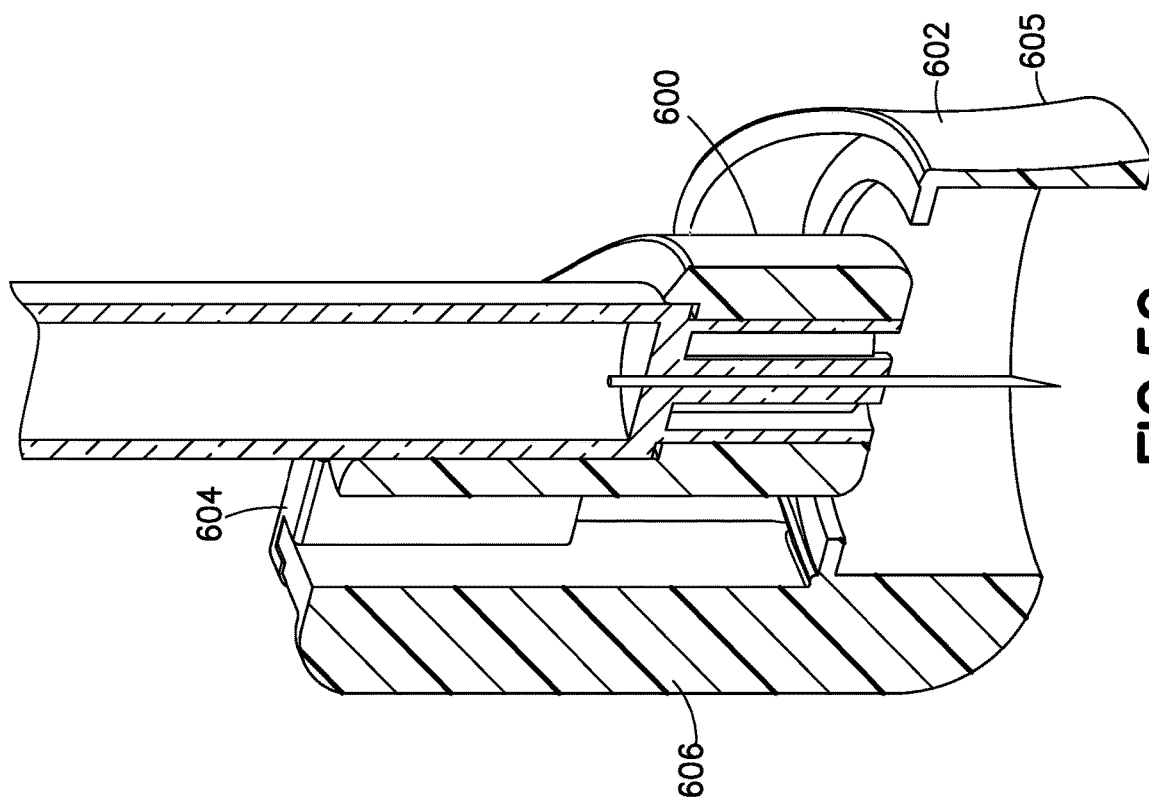
FIGS. 58-62 are partial elevational and partial cross-sectional views of the syringe of FIG. 57 illustrating operation thereof.
Figure 58:
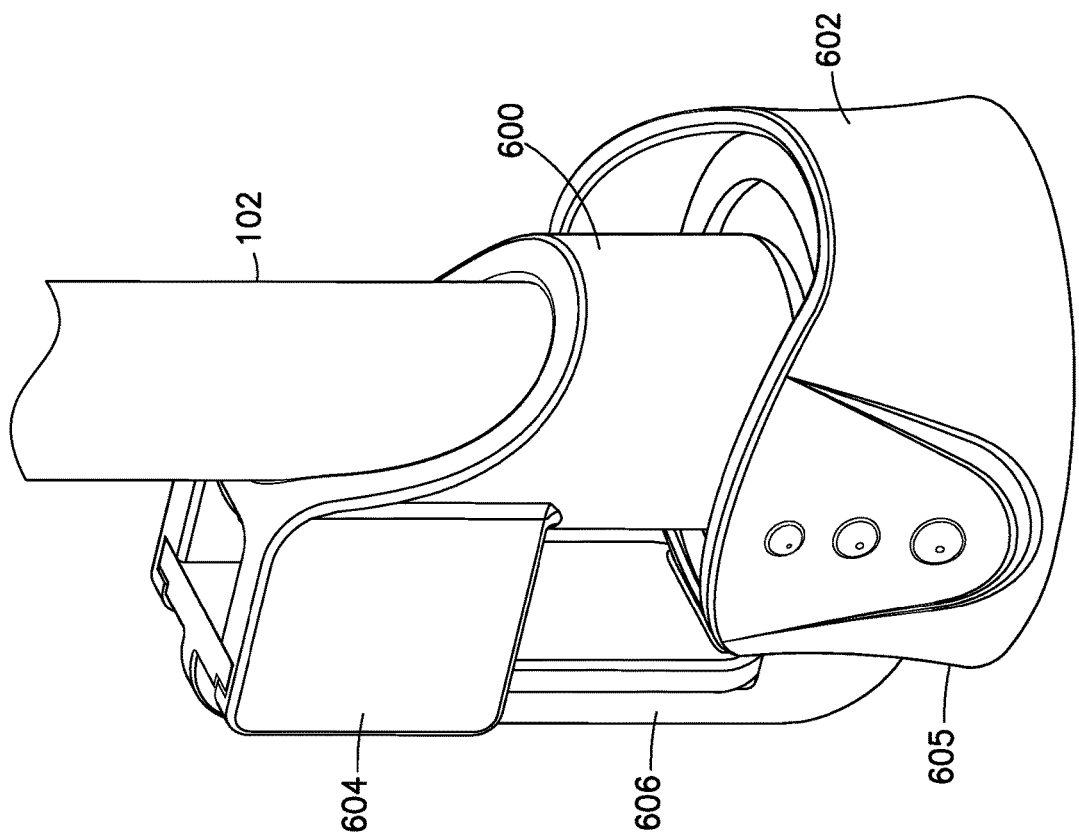

Similar to the embodiment of FIGS. 45-52, the embodiment of FIGS. 57-62 includes a sliding vial adapter. As shown in FIGS. 57-59, the syringe 100 includes a vial adapter 602 configured to slide relative to the needle adapter 600 along an axis substantially parallel to the longitudinal axis of the needle 140.

Unlike the embodiment of FIGS. 45-52, however, in this embodiment, a guiding portion 604 is integrally formed as a unitary construction with the needle adapter 600 (best shown in FIGS. 58 and 59). The vial adapter 602 includes a sleeve portion 605 and an extension 606 configured to slidably engage with the guiding portion 604. Preferably, the guiding portion 604 includes a T-slot and the extension 606 includes a T-shaped member configured to slidably engage the T-slot. According to another embodiment, however, the guiding portion includes the T-shaped member and the extension includes the T-slot. According to one embodiment, the extension 606 also includes a user manipulation portion configured to aid user manipulation of the vial adapter 602.

Figure 61:
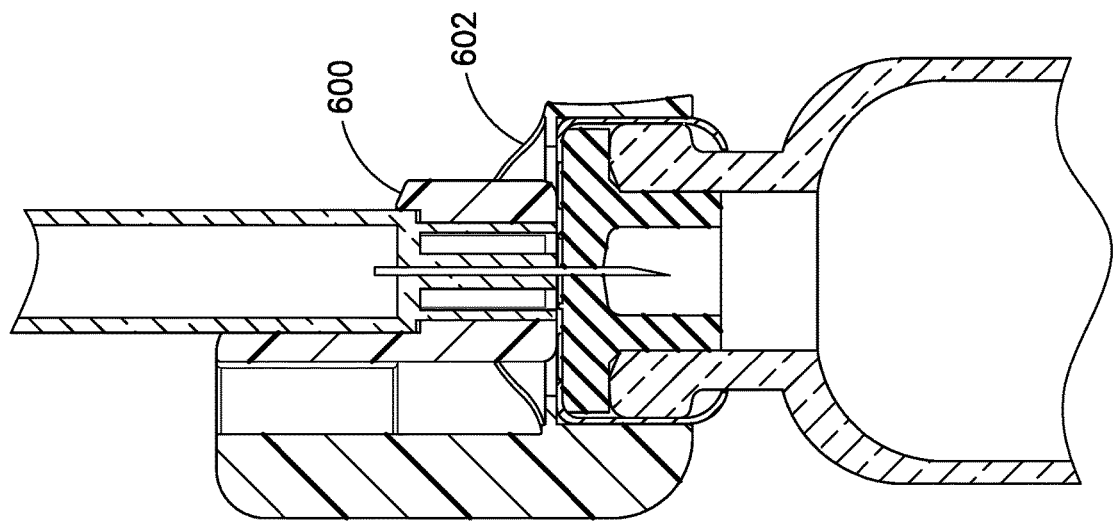
Figure 60:
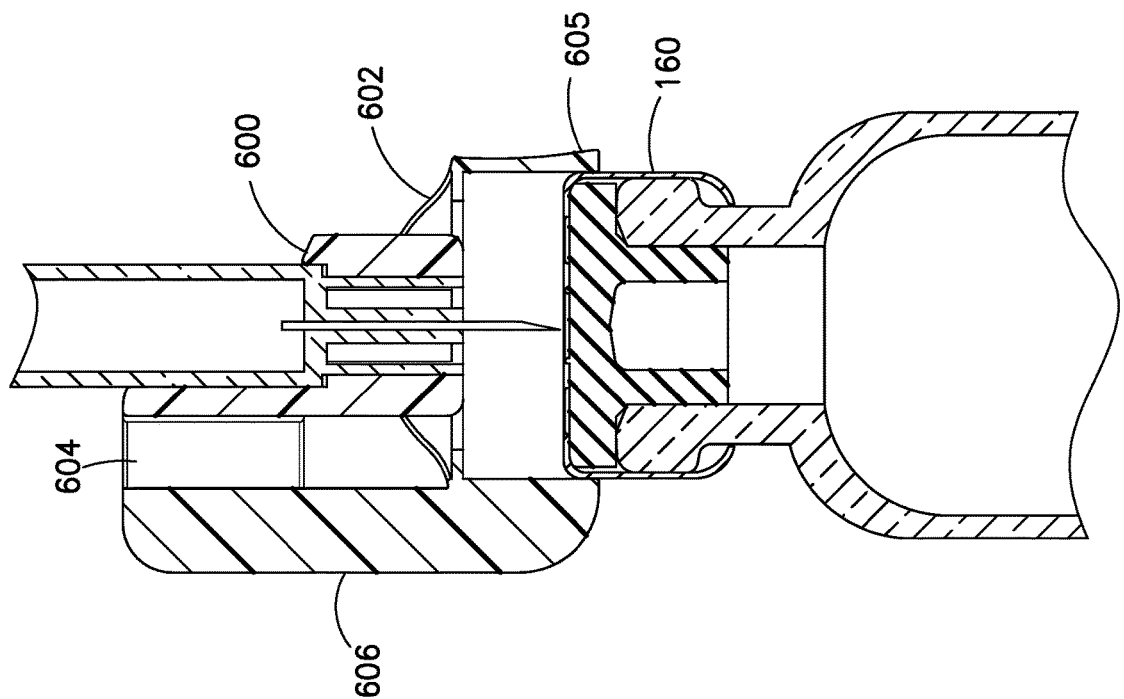
Figure 62:
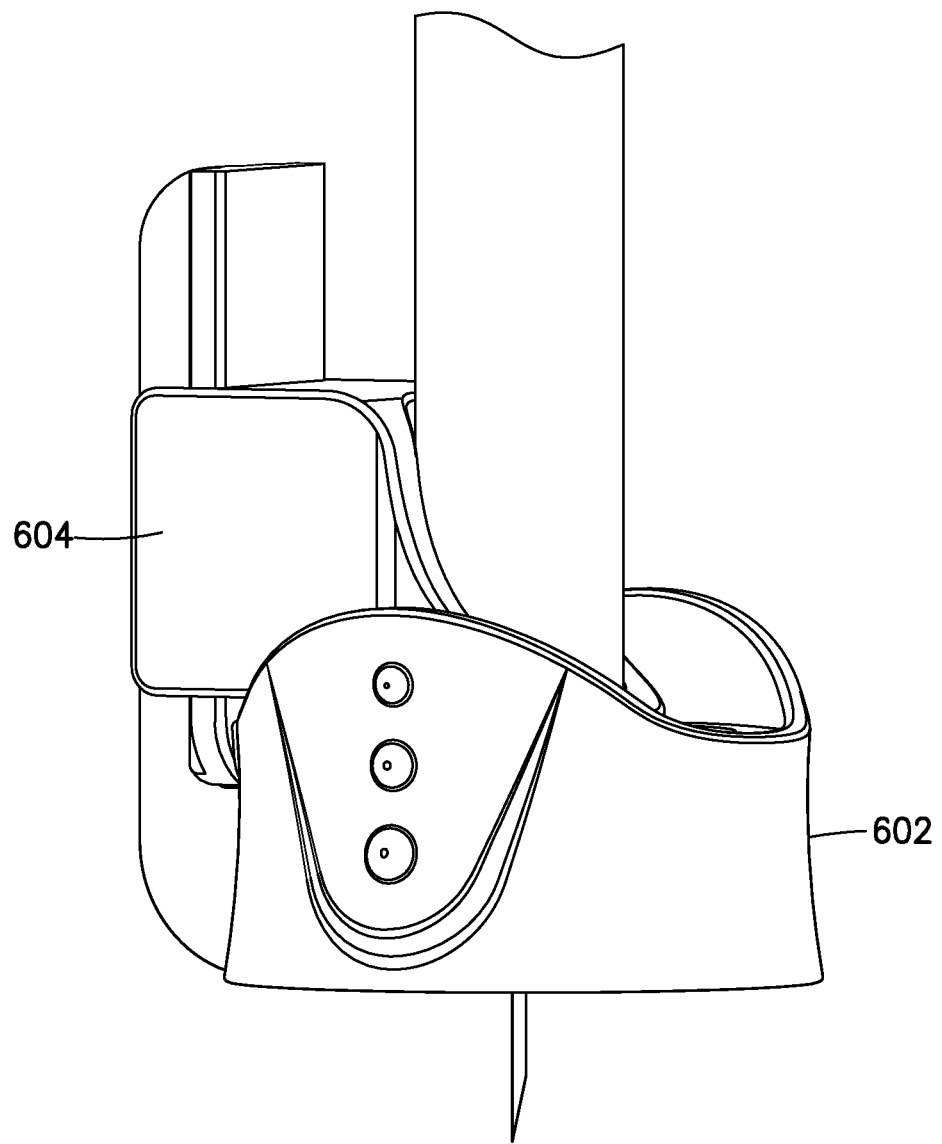
Figure 63:
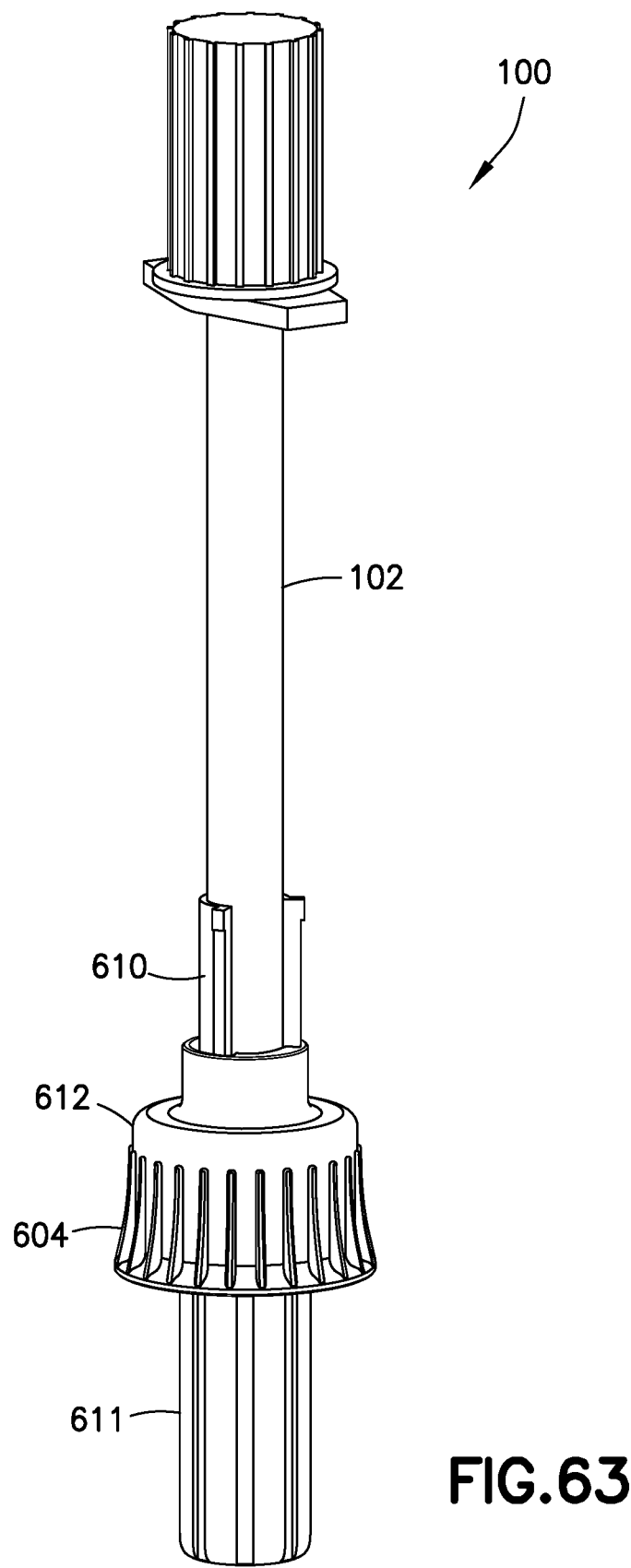
FIG. 63 is an elevational view of a syringe in accordance with another exemplary embodiment of the present invention.
Figure 64:
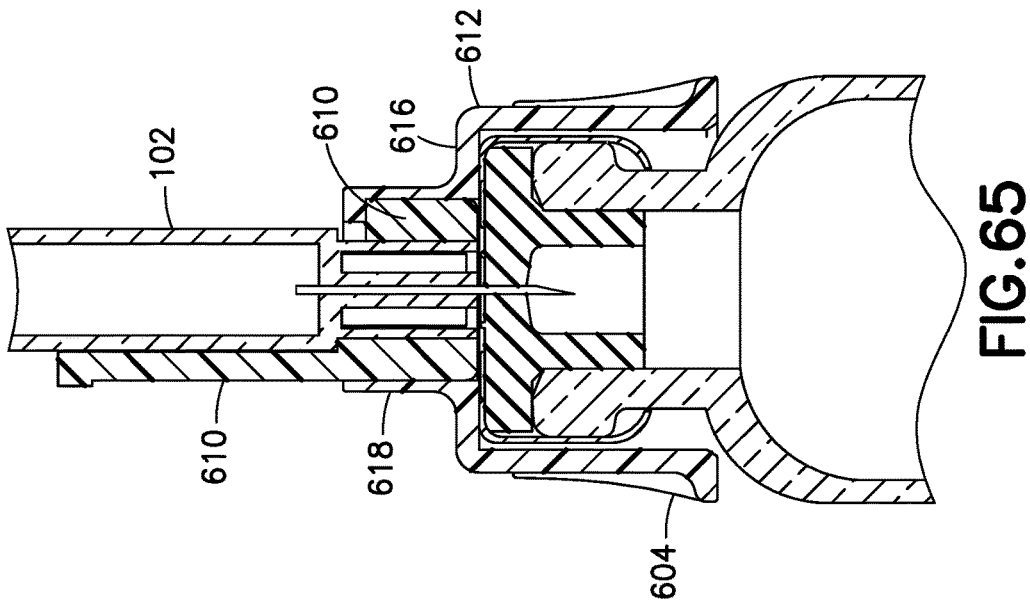
FIGS. 64-66 are partial cross-sectional and side views of the syringe of FIG. 63 illustrating operation thereof.

In operation, as shown in FIGS. 60-62, after removal of the needle cover 601 (FIG. 57), the user engages the vial adapter 602 with the vial stopper holder 160 (FIG. 60) (preferably by grasping the vial adapter 602), and continues pressing the vial adapter 602 distally toward the vial 150 until the sleeve portion 605 registers flush against the vial stopper holder 160 (FIG. 61). In this position, the vial adapter 572 engages the vial stopper holder 160 to aid central axial alignment of the needle 140 and the vial 150, and the substantially flat distal (distal-most) surface of the needle adapter 600 is flush with the vial stopper 165 to ensure that the tip of the needle 140 is properly inserted into the vial 150 to aspirate the medicament within the vial 150.

After aspiration of the medicament into the syringe barrel 102, the user removes the syringe 100 (including the needle adapter 600 and the vial adapter 602) from the vial 150, thereby readying the syringe 100 for injection.

According to one mode of operation, the contact of the vial adapter 602 on a patient's skin raises the vial adapter 602 relative to the needle adapter 600 as the needle 140 is inserted into the patient's skin. According to another mode of operation, the user lifts the vial adapter 602 relative to the needle adapter 600 prior to injection (FIG. 62).

In the embodiment of FIGS. 63-66, like the embodiment of FIGS. 40-44, the vial adapter 612 slides relative to the needle adapter 610. The needle adapter 610 has a substantially flat distal (distal-most) surface. A vial adapter or sleeve 612 is slidably connected to the needle adapter 610 and has a first end configured to removably receive the vial stopper holder 160. Preferably, the needle 140 is initially covered by a needle cover 611 (FIG. 63) that connects with the needle adapter 610 to ensure sterility of the needle 140 prior to use.

Preferably, the vial adapter 612 includes an radial flange 616 with an axial portion 618 configured to slidably grip the needle adapter 610. Also, preferably, the vial adapter includes one or more external gripping aids 604, such as axial splines 604.

Figure 65:
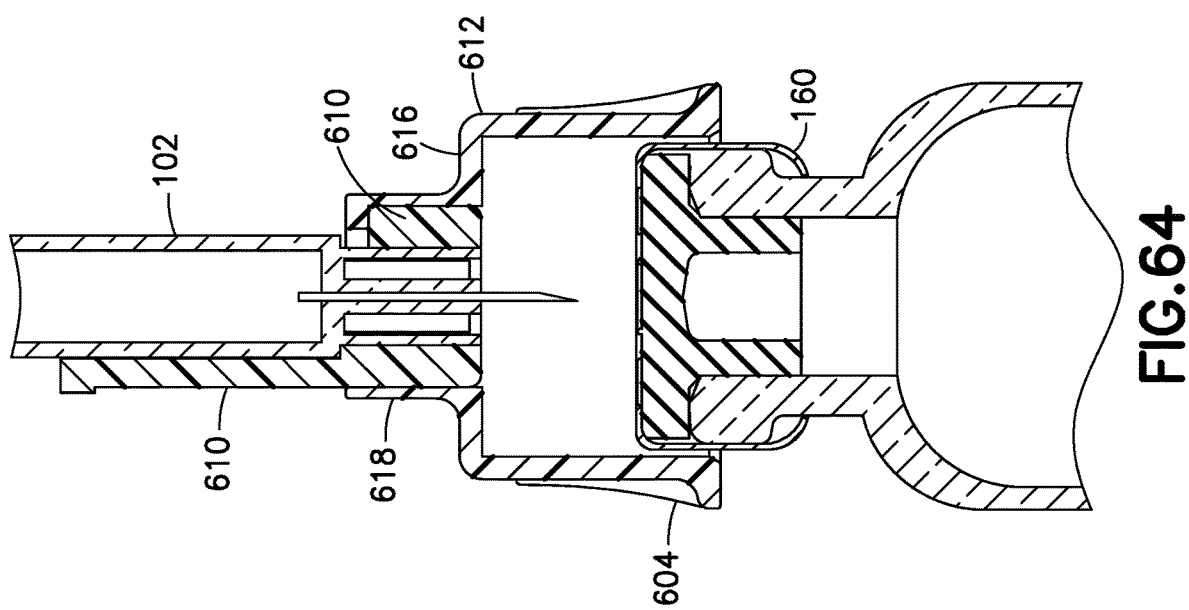

In operation, after removing the needle cover 611, the user engages the vial adapter 612 with the vial stopper holder 160 (FIG. 64) to aid central axial alignment of the needle 140 and the vial 150, preferably, by grasping the vial adapter 612 and pressing it toward the vial 150. The user continues to distally press the vial adapter toward the vial 150 until the substantially flat distal portion of the needle adapter 610 aligns flush with the vial stopper 165, to ensure that the tip of the needle 140 is properly inserted into the vial 150 to aspirate the medicament within the vial 150 (FIG. 65).

Figure 66:
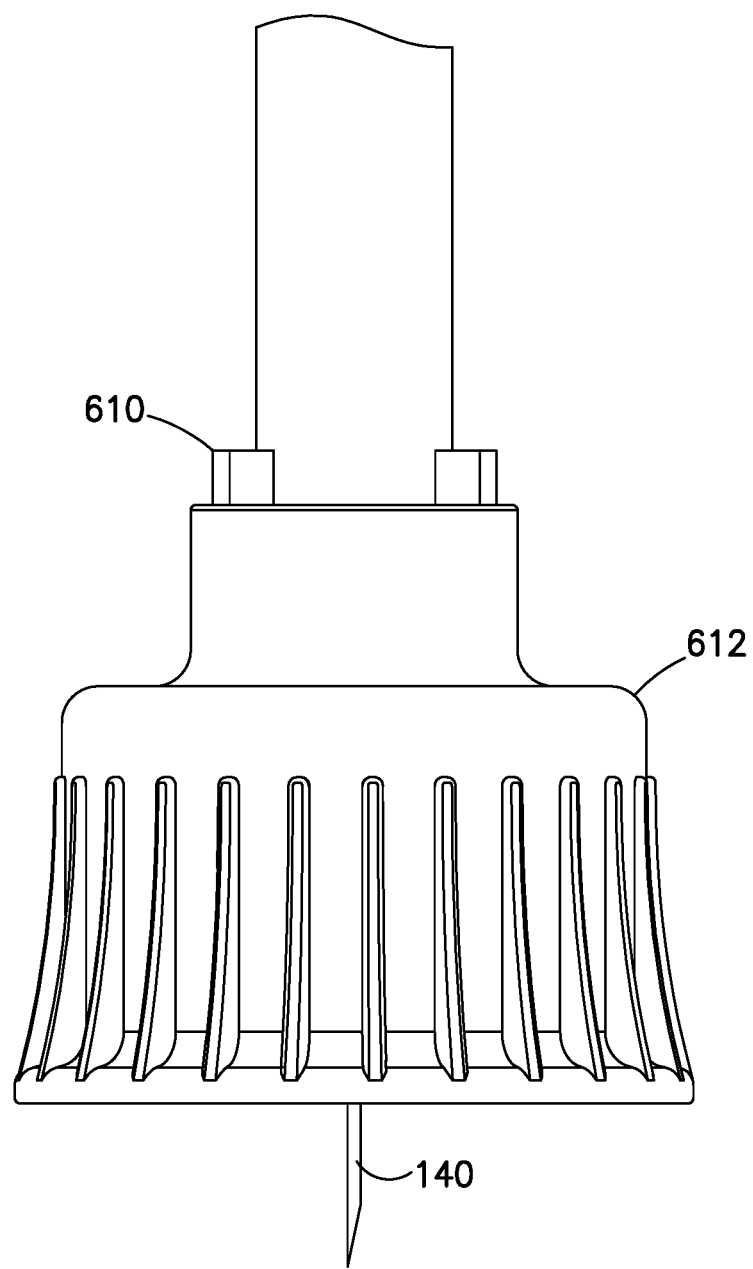

After aspiration of the medicament into the syringe barrel 102, the user removes the syringe 100 (including the vial adapter 612 and the needle adapter 610) from the vial 150. According to one embodiment, the syringe is now ready for injection, and the vial adapter 612 will slide proximally relative to the needle adapter 610 as the user inserts the needle 140 into the patient (FIG. 66). Alternatively, the user can manually slide the vial adapter 612 proximally relative to the needle adapter 610 to expose the needle 140 prior to injection (FIG. 66).

Figure 67:
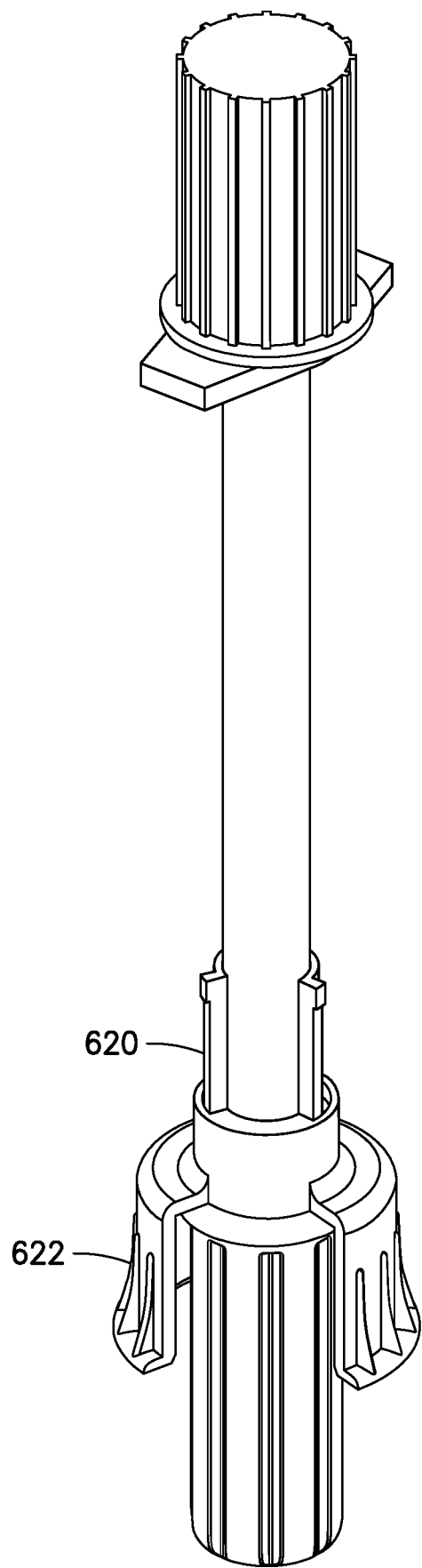
FIGS. 67 and 68 are elevational and partial elevational views of a syringe in accordance with another exemplary embodiment of the present invention.
Figure 68:
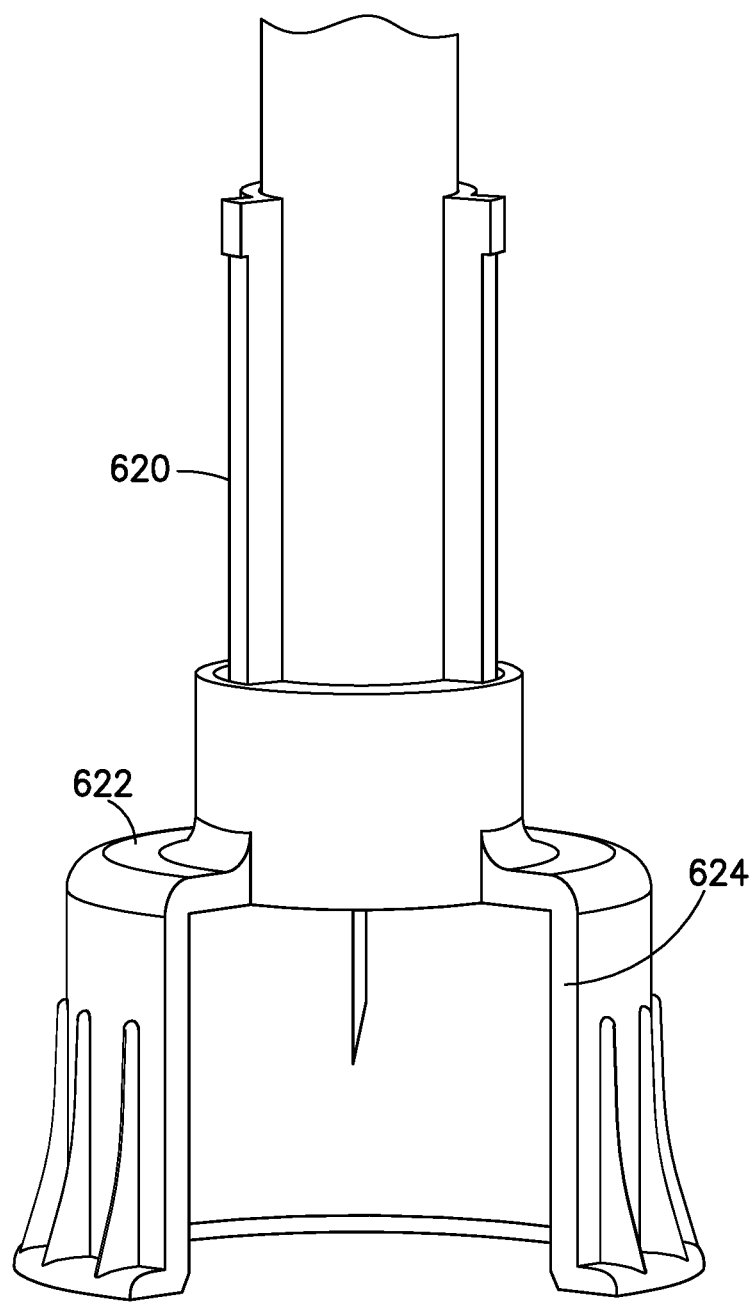

The embodiment if FIGS. 67 and 68 is substantially similar to the embodiment of FIGS. 63-67, except the vial adapter 622 has a cutaway portion 624, which enables a user to see the needle adapter 620 and the needle 140 more readily.

Preferably, the cutaway portion spans between 50 and 120 degrees of circumference. Most preferably, the cutaway portion spans about 60 degrees of circumference. According to one embodiment, the vial adapter has a plurality of cutaway portions. In such an embodiment, most preferably, the vial adapter has two cutaway portions opposite disposed about the vial adapter, with each cutaway portion spanning about 60 degrees of circumference.

Figure 69:
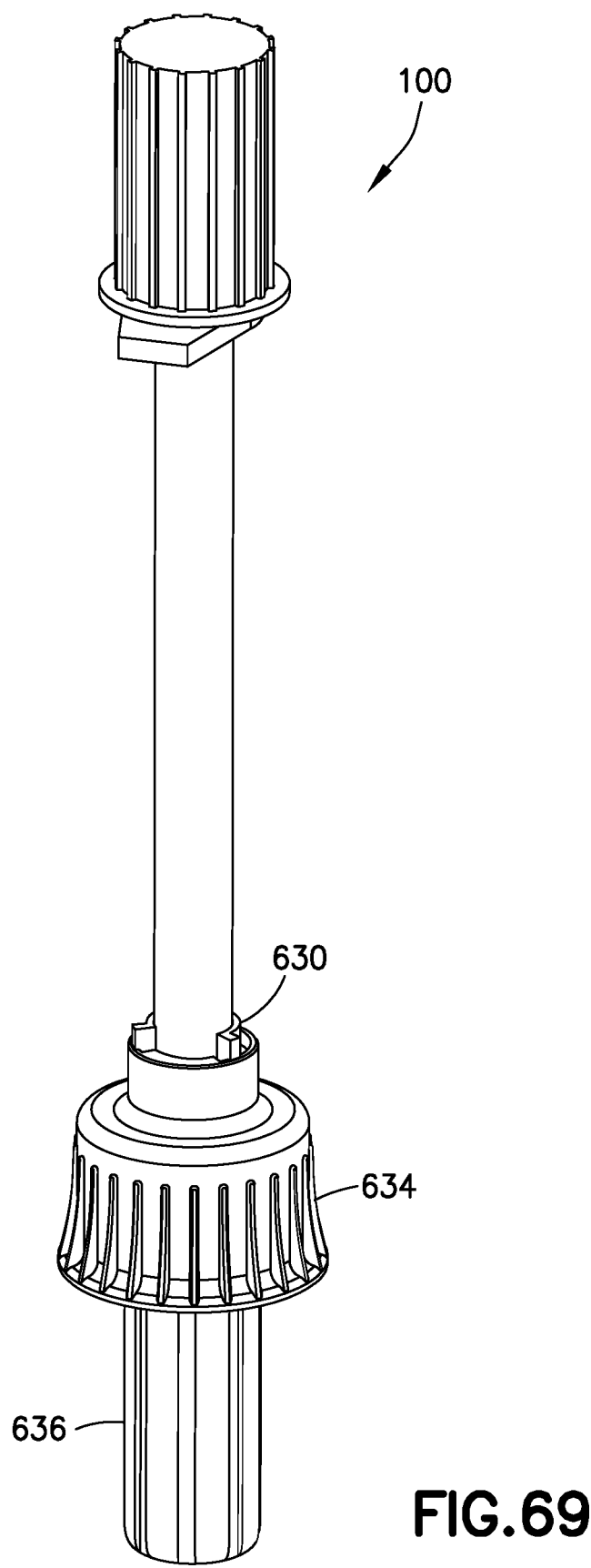
FIGS. 69 and 70 are elevational and partial elevational views of a syringe in accordance with another exemplary embodiment of the present invention.
Figure 70:
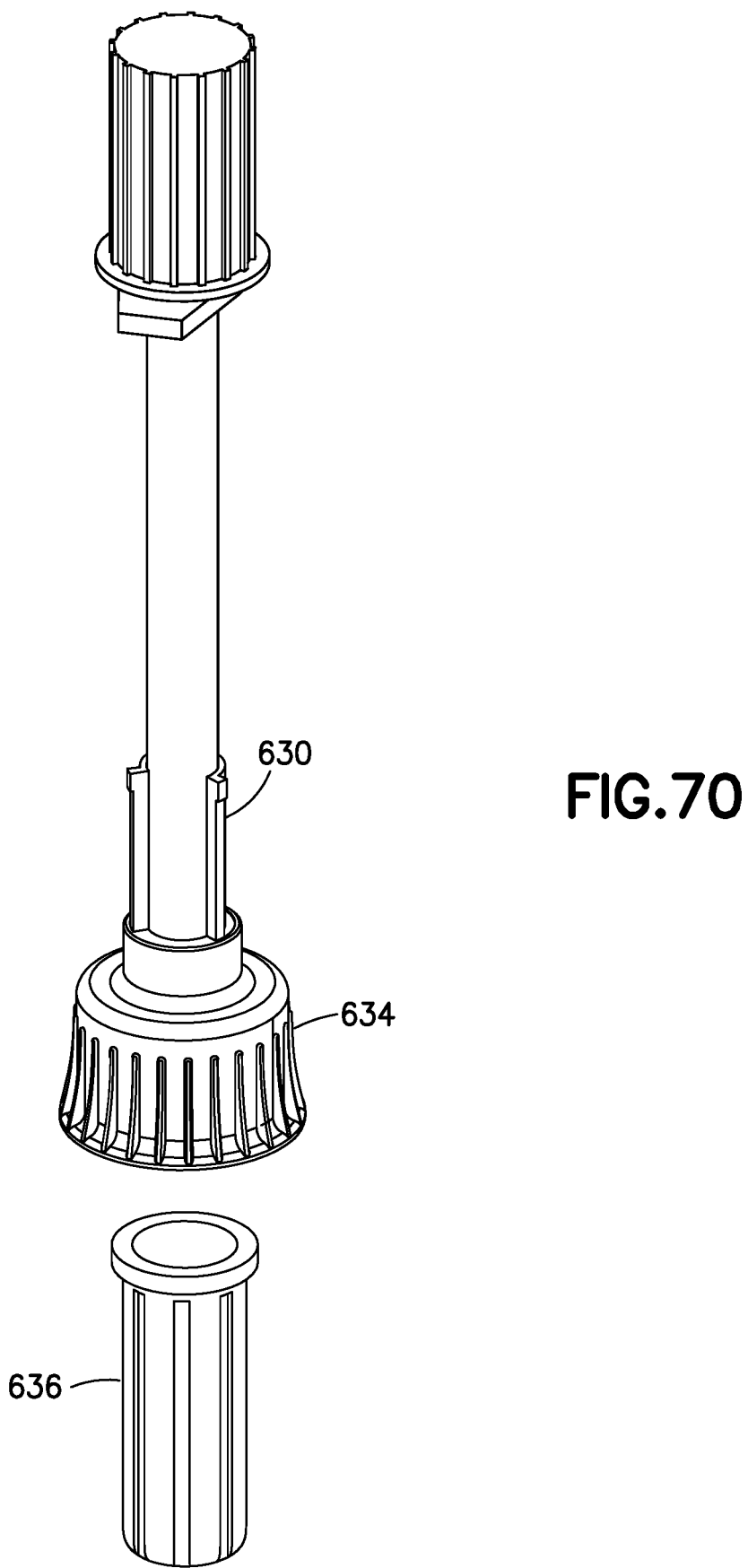

The embodiment of FIGS. 69 and 70 are similar to the embodiment of FIGS. 63-66, except the vial adapter 632 includes a sleeve portion 634 and a needle cover portion 636 that are integrally formed as a unitary structure. According to one embodiment, the needle cover portion 636 is frangibly connected to the sleeve portion 634 by sprues.

Initially, unlike the embodiment of FIGS. 63-66, the vial adapter 632 is disposed at a proximal portion of the needle adapter 630, as shown in FIG. 69. Preferably, the force required for removal of the needle cover portion 636 from the sleeve portion 634 slides the sleeve portion 634 distally relative to the needle adapter 630, as shown in FIG. 70. Subsequent to removal of the needle cover portion 636, the syringe 100 operates substantially similarly to the embodiment of FIGS. 63-66.

In the embodiments of FIGS. 16, 21, 25, and 32, the vial adapters removably engage the respective needle adapters. In the embodiments of FIGS. 16, 21, 25, 27, 32, and 40, the vial adapters simultaneously engage the respective needle adapters and the vial stopper holders.

It will be understood by one skilled in the art that in embodiments of the present invention, the needle adapter can be a separate part connected to the syringe body, or can be integrally formed with the syringe body as a unitary structure. For example, the needle adapter can be integrally formed as a unitary structure with the syringe barrel.

Embodiments of the present invention enable a 3.5-5 mm injection length syringe to reliably access the medication inside a medicament vial, for example, an insulin vial. Historically, syringe needle length has been limited by the ability of the needle tip to clear the rubber stopper portion of the medicament vial, particularly for stoppers that have a non-uniform cross-section. Embodiments of the present invention utilize a design feature on the syringe to provide a reliable method for inserting the syringe needle into the medicament vial so that the needle tip clears the vial stopper and accesses the medicament inside the vial.

Although only a few embodiments of the present invention have been shown and described, the present invention is not limited to the described embodiments. Instead, it will be appreciated by those skilled in the art that changes may be made to these embodiments without departing from the principles and spirit of the invention. It is particularly noted that those skilled in the art can readily combine the various technical aspects of the various elements of the various exemplary embodiments that have been described above in numerous other ways, all of which are considered to be within the scope of the invention, which is defined by the appended claims and their equivalents.

The invention claimed is:

1. A syringe, comprising:
   a syringe body having a syringe barrel configured to receive and administer a medicament;
   a hollow needle fluidly communicating with the syringe barrel; and
   a needle adapter disposed on the syringe body, an outer diameter of the needle adapter being wider than an outer diameter of the syringe barrel, and a distal surface of the needle adapter being substantially flat;
   wherein the needle adapter facilitates a flush alignment of the distal surface of the needle adapter with at least one of a vial stopper and a vial stopper holder of a medicament vial to ensure that a tip of the needle is properly inserted into the vial to aspirate the medicament within the vial, wherein the needle adapter comprises a first well having an inner wall and outer wall, wherein a height of the inner wall relative to the syringe body is the same as a height of the outer wall relative to the syringe body.

2. The syringe according to claim 1, wherein the inner wall includes a second well and the needle is mounted in the second well with an adhesive.

3. The syringe according to claim 1, wherein the first well includes a retention ring on an outer surface of the inner or outer wall.

4. The syringe according to claim 3, including a needle shield removably mounted to the retention ring.

5. The syringe according to claim 1, further comprising a vial adapter connected to the syringe and configured to engage a portion of the medicament vial to aid central axial alignment of the needle and the medicament vial.

6. The syringe according to claim 5, wherein the vial adapter removably engages the needle adapter.

7. The syringe according to claim 6, wherein the vial adapter enshrouds at least a majority of a perimeter of the vial stopper holder.

8. The syringe according to claim 7, wherein the vial adapter comprises a sleeve removably connectable to the needle adapter at a first end of the sleeve and connectable to the medicament vial to receive the vial stopper holder at a second end of the sleeve.

9. The syringe according to claim 7, further comprising a peel tab configured to removably cover one of the first and second ends of the sleeve to maintain sterility of the needle.

10. The syringe according to claim 7, wherein the sleeve is initially mounted on the needle adapter.

11. The syringe according to claim 7, further comprising a needle cover frangibly connected to the sleeve.

12. The syringe according to claim 7, wherein the sleeve is initially mounted on a plunger end of the syringe.

13. The syringe according to claim 7, wherein the vial adapter includes a flared end configured to receive the medicament vial and center the medicament vial to aid the central axial alignment of the needle and the medicament vial.

14. The syringe according to claim 5, wherein the vial adapter is connected to the needle adapter by a hinge.

15. The syringe according to claim 14, wherein the hinge is a bi-stable hinge.

16. The syringe according to claim 5, wherein the vial adapter slides relative to the needle adapter.

17. The syringe according to claim 13, wherein the vial adapter slides relative to the needle adapter along an axis substantially parallel to a longitudinal axis of the needle; and
   the vial adapter comprises:
      a sliding guide portion configured to slide along the syringe barrel; and
      a clip portion fixedly connected with the sliding guide portion and being configured to laterally clip onto a neck portion of the medicament vial.

18. The syringe according to claim 13, wherein the vial adapter comprises a sleeve slidably connected to the needle adapter and having a first end configured to removably receive the vial stopper holder of the medicament vial.

19. The syringe according to claim 13, wherein:
   the vial adapter slides relative to the needle adapter along an axis substantially parallel to a longitudinal axis of the needle;
   the syringe further comprises a guiding member fixedly disposed on the needle adapter; and the vial adapter comprises an extension slidably engaged with the guiding member.

20. The syringe according to claim 19, wherein one of the guiding member and the extension comprises a T-slot, and the remaining one of the guiding member and the extension comprises a T-shaped member slidably engaged with the T-slot.

21. The syringe according to claim 13, wherein:
the vial adapter slides relative to the needle adapter along an axis substantially parallel to a longitudinal axis of the needle;
the needle adapter comprises a guiding portion; and
the vial adapter comprises an extension slidably engaged with the guiding portion.

22. The syringe according to claim 21, wherein one of the guiding portion and the extension comprises a T-slot, and the remaining one of the guiding portion and the extension comprises a T-shaped member slidably engaged with the T-slot.

23. The syringe according to claim 5, wherein the vial adapter simultaneously engages the needle adapter and the vial stopper holder.

24. The syringe according to claim 1, further comprising a removable needle cover configured to maintain sterility of the needle.

25. The syringe according to claim 1, wherein the needle adapter and the syringe barrel are integrally formed as a unitary structure.

\* \* \* \* \*